(12) United States Patent
Quirk

(10) Patent No.: US 6,822,073 B2
(45) Date of Patent: Nov. 23, 2004

(54) MODULAR PEPTIDE-BASED REAGENT

(75) Inventor: Stephen Quirk, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 64 days.

(21) Appl. No.: 10/027,038

(22) Filed: Dec. 20, 2001

(65) Prior Publication Data

US 2003/0158380 A1 Aug. 21, 2003

(51) Int. Cl.[7] .............................................. A61K 38/16
(52) U.S. Cl. ...................................................... 530/324
(58) Field of Search ........................................ 530/324

(56) References Cited

U.S. PATENT DOCUMENTS

| | | | |
|---|---|---|---|
| 5,362,447 A | 11/1994 | Nokihara | 422/131 |
| 5,612,454 A | 3/1997 | Kaminuma et al. | 530/344 |
| 6,269,312 B1 | 7/2001 | Mayo et al. | 702/19 |

FOREIGN PATENT DOCUMENTS

| | | | |
|---|---|---|---|
| WO | WO-00/69900 | 11/2000 | C07K/1/107 |

OTHER PUBLICATIONS

Bjornholm, Berith, et al., "Conservation of a helix–stabilizing dipole moment in the PP–fold family of regulatory peptides.", *Biochemistry.* 32(12), (1993), 2954–2959.
Blundell, T.L., et al., "X–Ray analysis 1.4 angstrom resolution of avian pancreatic poly peptide small globular hormone.", *Proceedings of the National Academy of Sciences of the United States of America.* 78(7), (1981), 4175–4179.
Cerda–Reverter, Jose M., et al., "Neuropeptide Y family of peptides: Structure, anatomical expression, function, and molecular evolution.", *Biochemistry & Cell Biology.* 78(3), (2000), 371–392.
Chang, Paul J., et al., "Reversible dimerization of avian pancreatic poly peptide.", *Biochemistry.* 19(9), (1980), 1844–1849.
Fuhlendorff, Jannie, et al., "The antiparallel pancreatic polypeptide fold in the binding of neuropeptide Y to Y1 and Y2 receptors.", *Journal of Biological Chemistry.* 265(20), (1990), 11706–12.
Gehlert, Donald R., et al., "Characterization of the peptide binding requirements for the cloned human pancreatic polypeptide–preferring receptor.", *Molecular Pharmacology.* 50(1), (1996), 112–118.
Gingerich, Ronald L., et al., "Structural requirements of pancreatic polypeptide receptor binding.", *American Journal of Physiology.* 261(3 Pt 1), (1991), E319–324.
Glover, Ian, et al., "Conformational flexibility in a small globular hormone: x–ray analysis of avian pancreatic polypeptide at 0.98–A resolution.", *Biopolymers.* 22(1), (1983), 293–304.
Griko, Yuri V., et al., "Purification and characterization of human pancreatic polypeptide expressed in E. coli.", *Biochemical & Biophysical Research Communications.* 213(1), (1995), 239–248.
Hazelwood, Robert L., "Pancreatic polypeptide (PP) and its relevant relatives.", *Progress in Clinical & Biological Research.* 342, (1990), 250–256.
Kanazawa, Ikuo, et al., "Unfolding by temperature and guanidine hydrochloride of chicken pancreatic polypeptide.", *Journal of Biochemistry.* 100(1), (1986), 207–212.
Kruger, P., et al., "A comparison of the structure and dynamics of avian pancreatic polypeptide hormone in solution and in the crystal.", *European Biophysics Journal.* 13(2), (1985),77–88.
Noelken, Milton E., et al., "Conformation and association of pancreatic polypeptide from three species.", *Biochemistry.* 19(9), (1980), 1838–1843.
Wood, Stephen P., et al., "Purification, crystallisation and preliminary X–ray studies on avian pancreatic polypeptide.", *European Journal of Biochemistry.* 78(1), (1977),1 19–126.
Zondlo, Neal J., et al., "Highly Specific DNA Recognition by a Designed Miniature Protein", *J. Am. Chem. Soc.; (Communication)*; 121(29), (1999),6938–6939.
Desjarles, John R., et al., "De novo design of the hydrophobic cores of proteins", *Protein Science.* 4: 2006–2018. Cambridge University Press,(1995), 24 pgs.
Gulukota, Kamalakar , et al., "Two Complimentary Methods for Predicting Peptides Binding Major Histocompatibility Complex Molecules", *Journal of Molecular Biology*, 267, (1997), 125–1267.
Kono, Hidetoshi , et al., "Energy Minimization Method Using Automata Network for Sequence and Side–Chain Conformation Prediction From Given Backbone Geometry", *Proteins: Structure, Function, and Genetics*, 19,(1994), 244–255.
Wu, H. , et al., "Building Zinc Fingers by Selection: Toward a Therapeutic Application", *Proc. Natl. Acad. Sci., USA. Biochemistry.* 92. (Jan. 1995), 344–348.
*Database PIR73*, Accession No.: A28578 No. 19, (Nov. 19, 1988), 1 page.

Primary Examiner—Michael Borin
(74) Attorney, Agent, or Firm—Schwegman, Lundberg, Woessner & Kluth, P.A.

(57) ABSTRACT

The invention provides stable peptide backbones into which one or interactive domains may be incorporated. Such interactive domains may be specific binding domains, inhibitor domains, linkers, labels, solid supports, reactive sites, catalytic sites, useful chemical entities, and reagents. Attachment or incorporation of an interactive domain into the peptide backbone generates a peptide-based reagent. The invention also provides methods for generating libraries of peptides that can be used as interactive domains

9 Claims, 15 Drawing Sheets

```
M   C   P   S   Q   P   T   Y   P   G   D   P   G   P
ATG TGC CCG AGC CAG CCG ACC TAT CCG GGC GAT CCC GGG CCG

V   E   D   L   I   R   F   Y   D   N   L   Q   Q   W
GTG GAA GAT CTG ATC CGC TTT TAT GAT AAC CTG CAG CAG TGG

L   N   C   V   T   A   A   C   *
CTG AAC TGC GTG ACC GCC GCC TGC TAG
```

FIGURE 1

```
1           11          21          31          41
ACACACCATA  TGTGCCCGAG  CCAGCCGACC  TATCCGGGCG  ATCCCGGGCC
TGTGTGGTAT  ACACGGGCTC  GGTCGGCTGG  ATAGGCCCGC  TAGGGCCCGG 51          61          71          81          91
GGTGGAAGAT  CTGATCCGCT  TTTATGATAA  CCTGCAGCAG  TGGCTGAACT
CCACCTTCTA  GACTAGGCGA  AAATACTATT  GGACGTCGTC  ACCGACTTGA 101         111         121         131
GCGTGACCGC  CGCCTGCTAG  GGATCCACAC  AC
CGCACTGGCG  GCGGACGATC  CCTAGGTGTG  TG
```

FIGURE 2

SEQUENCE LISTING

<160> NUMBER OF SEQ ID NOS: 34

<210> SEQ ID NO 1
<211> LENGTH: 36
<212> TYPE: PRT
<213> ORGANISM: Meleagris gallopavo -continued

```
<400> SEQUENCE: 1

Gly Pro Ser Gln Pro Thr Tyr Pro Gly Asp Asp Ala Pro Val Glu Asp
 1               5                  10                  15

Leu Ile Arg Phe Tyr Asp Asn Leu Gln Gln Tyr Leu Asn Val Val Thr
            20                  25                  30

Arg His Arg Tyr
         35

<210> SEQ ID NO 2
<211> LENGTH: 36
<212> TYPE: PRT
<213> ORGANISM: Artificial Sequence
<220> FEATURE:
<223> OTHER INFORMATION: A peptide backbone.

<400> SEQUENCE: 2

Gly Pro Ser Gln Pro Thr Tyr Pro Gly Asp Asp Ala Pro Val Glu Asp
 1               5                  10                  15

Leu Ile Arg Phe Tyr Asp Asn Leu Gln Gln Trp Leu Asn Val Val Thr
            20                  25                  30

Arg His Arg Tyr
         35

<210> SEQ ID NO 3
<211> LENGTH: 37
<212> TYPE: PRT
<213> ORGANISM: Artificial Sequence
<220> FEATURE:
<223> OTHER INFORMATION: A peptide backbone.

<400> SEQUENCE: 3

Met Cys Pro Ser Gln Pro Thr Tyr Pro Gly Asp Asp Ala Pro Val Glu
 1               5                  10                  15

Asp Leu Ile Arg Phe Tyr Asp Asn Leu Gln Gln Tyr Leu Asn Val Val
            20                  25                  30

Thr Arg His Arg Tyr
         35

<210> SEQ ID NO 4
<211> LENGTH: 37
<212> TYPE: PRT
<213> ORGANISM: Artificial Sequence
<220> FEATURE:
<223> OTHER INFORMATION: A peptide backbone.

<400> SEQUENCE: 4

Met Cys Pro Ser Gln Pro Thr Tyr Pro Gly Asp Asp Ala Pro Val Glu
 1               5                  10                  15

Asp Leu Ile Arg Phe Tyr Asp Asn Leu Gln Gln Tyr Leu Asn Cys Val
            20                  25                  30

Thr Arg His Arg Tyr
         35

<210> SEQ ID NO 5
<211> LENGTH: 36
<212> TYPE: PRT
<213> ORGANISM: Artificial Sequence
<220> FEATURE:
<223> OTHER INFORMATION: A peptide backbone.

<400> SEQUENCE: 5

Gly Pro Ser Gln Pro Thr Tyr Pro Gly Asp Pro Ala Pro Val Glu Asp
```

```
                 1               5                  10                 15
Leu Ile Arg Phe Tyr Asp Asn Leu Gln Gln Tyr Leu Asn Val Val Thr
            20                  25                 30

Arg His Arg Tyr
        35

<210> SEQ ID NO 6
<211> LENGTH: 36
<212> TYPE: PRT
<213> ORGANISM: Artificial Sequence
<220> FEATURE:
<223> OTHER INFORMATION: A peptide backbone.

<400> SEQUENCE: 6

Gly Pro Ser Gln Pro Thr Tyr Pro Gly Asp Asp Gly Pro Val Glu Asp
 1               5                  10                 15

Leu Ile Arg Phe Tyr Asp Asn Leu Gln Gln Tyr Leu Asn Val Val Thr
            20                  25                 30

Arg His Arg Tyr
        35

<210> SEQ ID NO 7
<211> LENGTH: 4
<212> TYPE: PRT
<213> ORGANISM: Meleagris gallopavo

<400> SEQUENCE: 7

Arg His Arg Tyr
 1

<210> SEQ ID NO 8
<211> LENGTH: 34
<212> TYPE: PRT
<213> ORGANISM: Artificial Sequence
<220> FEATURE:
<223> OTHER INFORMATION: A peptide backbone.

<400> SEQUENCE: 8

Gly Pro Ser Gln Pro Thr Tyr Pro Gly Asp Asp Ala Pro Val Glu Asp
 1               5                  10                 15

Leu Ile Arg Phe Tyr Asp Asn Leu Gln Gln Tyr Leu Asn Val Val Thr
            20                  25                 30

Ala Ala

<210> SEQ ID NO 9
<211> LENGTH: 37
<212> TYPE: PRT
<213> ORGANISM: Artificial Sequence
<220> FEATURE:
<223> OTHER INFORMATION: A peptide backbone.

<400> SEQUENCE: 9

Gly Pro Ser Gln Pro Thr Tyr Pro Gly Asp Asp Ala Pro Val Glu Asp
 1               5                  10                 15

Leu Ile Arg Phe Tyr Asp Asn Leu Gln Gln Tyr Leu Asn Val Val Thr
            20                  25                 30

Arg His Arg Tyr Cys
        35

<210> SEQ ID NO 10
<211> LENGTH: 33
<212> TYPE: PRT
```

```
<213> ORGANISM: Artificial Sequence
<220> FEATURE:
<223> OTHER INFORMATION: A peptide backbone.

<400> SEQUENCE: 10

Gly Pro Ser Gln Pro Thr Tyr Pro Gly Asp Asp Ala Pro Val Glu Asp
 1               5                  10                  15

Leu Ile Arg Phe Tyr Asp Asn Leu Gln Gln Tyr Leu Asn Val Val Thr
            20                  25                  30

Cys

<210> SEQ ID NO 11
<211> LENGTH: 36
<212> TYPE: PRT
<213> ORGANISM: Artificial Sequence
<220> FEATURE:
<223> OTHER INFORMATION: A peptide backbone.

<400> SEQUENCE: 11

Met Cys Pro Ser Gln Pro Thr Tyr Pro Gly Asp Pro Gly Pro Val Glu
 1               5                  10                  15

Asp Leu Ile Arg Phe Tyr Asp Asn Leu Gln Gln Trp Leu Asn Cys Val
            20                  25                  30

Thr Ala Ala Cys
        35

<210> SEQ ID NO 12
<211> LENGTH: 111
<212> TYPE: DNA
<213> ORGANISM: Artificial Sequence
<220> FEATURE:
<223> OTHER INFORMATION: A nucleotide sequence encoding SEQ ID NO:11.

<400> SEQUENCE: 12
atgtgcccga gccagccgac ctatccgggc gatcccgggc cggtggaaga tctgatccgc      60
ttttatgata acctgcagca gtggctgaac tgcgtgaccg ccgcctgcta g              111

<210> SEQ ID NO 13
<211> LENGTH: 132
<212> TYPE: DNA
<213> ORGANISM: Artificial Sequence
<220> FEATURE:
<223> OTHER INFORMATION: A nucleotide sequence encoding SEQ ID NO:11.

<400> SEQUENCE: 13
acacaccata tgtgcccgag ccagccgacc tatccgggcg atcccgggcc ggtggaagat      60
ctgatccgct tttatgataa cctgcagcag tggctgaact gcgtgaccgc cgcctgctag     120
ggatccacac ac                                                         132

<210> SEQ ID NO 14
<211> LENGTH: 35
<212> TYPE: PRT
<213> ORGANISM: Artificial Sequence
<220> FEATURE:
<223> OTHER INFORMATION: A peptide backbone.

<400> SEQUENCE: 14

Cys Pro Ser Gln Pro Thr Tyr Pro Gly Asp Pro Gly Pro Val Glu Asp
 1               5                  10                  15

Leu Ile Arg Phe Tyr Asp Asn Leu Gln Gln Trp Leu Asn Cys Val Thr
            20                  25                  30
```

-continued

```
Ala Ala Cys
        35

<210> SEQ ID NO 15
<211> LENGTH: 6
<212> TYPE: PRT
<213> ORGANISM: Bos taurus

<400> SEQUENCE: 15

Pro Tyr Arg Ile Arg Phe
 1               5

<210> SEQ ID NO 16
<211> LENGTH: 18
<212> TYPE: DNA
<213> ORGANISM: Artificial Sequence
<220> FEATURE:
<223> OTHER INFORMATION: A portion of the recognition sequence from
      Bovine Pancreatic Trypsin Inhibitor (PYRIRF, SEQ ID
      NO:15) converted into this DNA sequence using E.
      coli codon usage.

<400> SEQUENCE: 16
ccgtatcgca tccgcttt                                                 18

<210> SEQ ID NO 17
<211> LENGTH: 30
<212> TYPE: DNA
<213> ORGANISM: Artificial Sequence
<220> FEATURE:
<223> OTHER INFORMATION: SEQ ID NO:16 with flanking Sma I sites.

<400> SEQUENCE: 17
cccgggccgt atcgcatccg ctttcccggg                                    30

<210> SEQ ID NO 18
<211> LENGTH: 5
<212> TYPE: PRT
<213> ORGANISM: Artificial Sequence
<220> FEATURE:
<223> OTHER INFORMATION: A peptide interactive domain.

<400> SEQUENCE: 18

Tyr Lys Leu Lys Tyr
 1               5

<210> SEQ ID NO 19
<211> LENGTH: 15
<212> TYPE: DNA
<213> ORGANISM: Artificial Sequence
<220> FEATURE:
<223> OTHER INFORMATION: SEQ ID NO:18 converted into this DNA sequence.

<400> SEQUENCE: 19
tataaactga agtat                                                    15

<210> SEQ ID NO 20
<211> LENGTH: 27
<212> TYPE: DNA
<213> ORGANISM: Artificial Sequence
<220> FEATURE:
<223> OTHER INFORMATION: SEQ ID NO:19 with Sma I flanking sequences.

<400> SEQUENCE: 20
cccgggtata aactgaagta tcccggg                                       27
```

<210> SEQ ID NO 21
<211> LENGTH: 41
<212> TYPE: PRT
<213> ORGANISM: Artificial Sequence
<220> FEATURE:
<223> OTHER INFORMATION: A peptide-based reagent that combines the
SEQ ID NO:15 interactive domain with the SEQ ID NO:11
peptide backbone.

<400> SEQUENCE: 21

Cys Pro Ser Gln Pro Thr Tyr Pro Gly Asp Pro Pro Tyr Arg Ile Arg
 1               5                  10                  15

Phe Gly Pro Val Glu Asp Leu Ile Arg Phe Tyr Asp Asn Leu Gln Gln
            20                  25                  30

Trp Leu Asn Cys Val Thr Ala Ala Cys
         35                  40

<210> SEQ ID NO 22
<211> LENGTH: 40
<212> TYPE: PRT
<213> ORGANISM: Artificial Sequence
<220> FEATURE:
<223> OTHER INFORMATION: A peptide-based reagent that combines the
SEQ ID NO:18 interactive domain with the SEQ ID NO:11
peptide backbone.

<400> SEQUENCE: 22

Cys Pro Ser Gln Pro Thr Tyr Pro Gly Asp Pro Tyr Lys Leu Lys Tyr
 1               5                  10                  15

Gly Pro Val Glu Asp Leu Ile Arg Phe Tyr Asp Asn Leu Gln Gln Trp
            20                  25                  30

Leu Asn Cys Val Thr Ala Ala Cys
         35                  40

<210> SEQ ID NO 23
<211> LENGTH: 20
<212> TYPE: DNA
<213> ORGANISM: Artificial Sequence
<220> FEATURE:
<223> OTHER INFORMATION: An oligonucleotide used to construct
SEQ ID NO:13.

<400> SEQUENCE: 23
acacaccata tgtgcccgag                                                     20

<210> SEQ ID NO 24
<211> LENGTH: 28
<212> TYPE: DNA
<213> ORGANISM: Artificial Sequence
<220> FEATURE:
<223> OTHER INFORMATION: An oligonucleotide used to construct
SEQ ID NO:13.

<400> SEQUENCE: 24
tcggctggct cgggcacata tggtgtgt                                            28

<210> SEQ ID NO 25
<211> LENGTH: 27
<212> TYPE: DNA
<213> ORGANISM: Artificial Sequence
<220> FEATURE:
<223> OTHER INFORMATION: An oligonucleotide used to construct
SEQ ID NO:13.

<400> SEQUENCE: 25
ccagccgacc tatccgggcg atcccgg                                             27

<210> SEQ ID NO 26
<211> LENGTH: 27
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 26
ccaccggccc gggatcgccc ggatagg                                27

<210> SEQ ID NO 27
<211> LENGTH: 28
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 27
gccggtggaa gatctgatcc gcttttat                              28

<210> SEQ ID NO 28
<211> LENGTH: 28
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 28
aggttatcat aaaagcggat cagatctt                              28

<210> SEQ ID NO 29
<211> LENGTH: 28
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 29
gataacctgc agcagtggct gaactgcg                              28

<210> SEQ ID NO 30
<211> LENGTH: 29
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 30
cggcggtcac gcagttcagc cactgctgc                             29

<210> SEQ ID NO 31
<211> LENGTH: 29
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 31
tgaccgccgc ctgctaggga tccacacac                             29

```
<210> SEQ ID NO 32
<211> LENGTH: 20
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 32
gtgtgtggat ccctagcagg                                                  20

<210> SEQ ID NO 33
<211> LENGTH: 18
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 33
acacaccata tgtgcccg                                                    18

<210> SEQ ID NO 34
<211> LENGTH: 18
<212> TYPE: DNA
<213> ORGANISM: Artificial Sequence
<220> FEATURE:
<223> OTHER INFORMATION: An oligonucleotide used to construct
      SEQ ID NO:13.

<400> SEQUENCE: 34
gtgtgtggat ccctagca                                                    18
```

MODULAR PEPTIDE-BASED REAGENT

FIELD OF THE INVENTION

The invention relates to peptides that have a stable backbone that can be readily adapted to provide a multitude of interactive domains such as inhibitory or binding domains.

BACKGROUND OF THE INVENTION

One drawback to immunologically based diagnostic assays is the reliance on the use of antibodies. These reagents, whether monoclonal or polyclonal, are large macromolecular polypeptides that are expensive to produce and often become unstable during storage, necessitating a short shelf life for many diagnostic products. In addition, a typical immunoglobin (e.g.-IgG) contains a great deal of mass (the Fc region) that is physiologically important, but that plays no role in antigen recognition. Such added mass is unnecessary for many applications and can add background noise, inhibit diffusion and cause side reactions. Moreover, the disulfide bonds holding heavy and light chains of antibodies together are potentially labile. Thus, only a small fraction of the antibody structure (and therefore mass) is directly involved in antigen recognition, yet the entirety of the antibody is often produced and used in a sensor or diagnostic device.

It is possible to produce smaller Fab regions from intact antibodies, but Fab production requires several chemical or enzymatic processing steps and additional protein purification procedures. Such processing procedures add significant costs to the diagnostic product.

What is needed is an easily synthesized, stable antigen recognition element, where a higher proportion of the molecular mass is involved in antigen recognition.

SUMMARY OF THE INVENTION

The invention provides easily synthesized, peptide backbones that can be readily modified to include binding domains, inhibitor domains, linkers, labels, reagents, reactive sites, catalytic sites or reagents and other chemical entities.

In one embodiment, the invention provides a stable isolated peptide comprising an amino acid sequence with at least 90% identity to any one of SEQ ID NO:2–6, 8–11 or 14. Such a stable isolated peptide can have a polyproline helix, a short loop region, and an alpha helix, where the peptide folds so that the polyproline helix and the alpha helix hydrophobically interact. Peptides of the invention are often more stable than a peptide having SEQ ID NO:1, which is a small peptide derived from Avian Pancreatic Polypeptide. Other peptides of the invention are less stable than a peptide having SEQ ID NO:1. Desirable peptides include an amino acid sequence with at least 90% identity to SEQ ID NO:11 or 14. Peptides having SEQ ID NO:11 or 14, are folded as described above and further stabilized by a disulfide bond.

The invention also provides isolated nucleic acids encoding a stable peptide comprising an amino acid sequence with at least 90% identity to any one of SEQ ID NO:2–6, 8–11 or 14. Preferably, the isolated nucleic acid encodes and amino acid sequence with at least 90% identity to any one of SEQ ID NO:11 or 14. Examples of such nucleic acids comprise SEQ ID NO:12 or 13.

In another embodiment, the invention provides a peptide-based reagent comprising a peptide backbone and an interactive domain, where the peptide backbone comprises an amino acid sequence with at least 90% identity to any one of SEQ ID NO:2–6, 8–11 or 14. Desirable peptide-based reagents have a peptide backbone and an interactive domain, where the peptide backbone comprises an amino acid sequence with at least 90% identity to SEQ ID NO:11 or 14. The peptide backbone can have a polyproline helix, a short loop region, and an alpha helix, where the peptide backbone folds so that the polyproline helix and the alpha helix hydrophobically interact. Desirable peptide backbones are more stable than a peptide having SEQ ID NO:1. Desirable peptide-based reagents are more stable than the peptide backbone that does not have the interactive domain. However, insertion of some interactive domains de-stabilizes the peptide backbone and such destabilized peptide-based reagents may still be useful to one of skill in the art.

The interactive domains for attachment onto, or insertion into, the peptide backbone can be any useful peptide or molecule chosen by one of skill in the art. Examples of interactive domains include binding domains, inhibitor domains, antigen-recognizing peptides, linkers, labels, solid supports, and enzymatic active sites. One peptide-based reagent of the invention has an interactive domain where the peptide comprises SEQ ID NO:18.

The invention also provides a method comprising:

defining a search zone comprising a site of interaction on a target protein to which a peptide can interact;

defining a size for the peptide;

defining a class of amino acids for each position in the amino acid sequence of the peptide;

substituting each member of a defined class of amino acids into each position of the amino acid sequence of the peptide sequence to generate an output library file comprising a plurality of output peptide sequences;

communicating the output library file to a molecular docking program to fit each of the plurality of output peptide sequences to the search zone and to create a target protein-peptide sequence fit score;

ranking the plurality of output peptides sequences by target protein-peptide sequence fit score; and displaying each of the plurality of output peptide sequences and its associated target protein-peptide sequence fit score;

wherein a portion of the plurality of output peptide sequences can stably interact with the target protein.

The search zone can include the x-, y-, and z-coordinates of each non-hydrogen atoms in the target protein. Output peptide sequences with higher target protein-peptide sequence fit scores can often bind with higher affinity to the target protein. The method can further include receiving an input percentage selection to limit the plurality of output peptide sequences to a certain percentage; wherein the input percentage selection is capable of limiting an output library file size and a library complexity. Each class of amino acids can separately comprise any one of genetically encoded L-amino acids, naturally occurring non-genetically encoded L-amino acids, synthetic L-amino acids, D-enantiomers of genetically encoded amino acids, D-enantiomers of naturally occurring non-genetically encoded amino acids, or synthetic D-amino acids. Each class of amino acids can also separately comprise any one of hydrophilic amino acids, hydrophobic amino acids, cysteine-like amino acids, acidic amino acids, basic amino acids, polar amino acids, aromatic amino acids, apolar amino acids or aliphatic amino acids. In one embodiment, the target protein is bovine pancreatic trypsin and one of the output peptide sequences is YKLKY (SEQ ID NO:18).

The invention is also directed to a system for creating peptide sequences, comprising: a processor; a memory coupled to the processor; a display couple to the processor; a make peptide sequence component capable of executing on the processor to generate peptide sequences; an output class component capable of executing on the processor to display each class of amino acid residues used by the make peptide sequence component; and an output peptide sequence component capable of executing on the processor to display peptide sequences. One example of a display is a printer. The output class component may be capable of displaying each class of amino acid residues used by the make peptide sequence component.

The invention further provides a machine-accessible medium having associated content capable of directing the machine to perform a method, the method comprising:

receiving a search zone comprising a plurality of coordinates for atoms in an target site to which a plurality of peptides can bind with varying affinities;

receiving a peptide length parameter comprising a number of amino acids;

receiving a defined class of amino acid structures to be analyzed for fitness at each position along the peptide length;

generating a output library file comprising a plurality of output peptide sequences containing each amino acid from each defined class of amino acid structures at each position along the peptide length;

sequentially translating and rotating each member of the class of amino acid structures at each position within a peptide relative to the search zone to sequentially create a peptide sequence with a target site-peptide sequence fit score;

ranking peptide sequences by target site-peptide sequence fit scores; and displaying a selected percentage of the target site-peptide sequence fit scores with the associated peptide sequences.

The method performed by the machine-accessible medium can further include displaying labels for the output peptide sequences and storing the search zone.

DESCRIPTION OF THE FIGURES

FIG. 1 provides a DNA (SEQ ID NO:12) and amino acid (SEQ ID NO:11) sequence of the SAP peptide. The asterisk denotes the stop codon. The codon selection is biased towards *E. coli*. The initial methionine is used if the SAP molecule is to be produced using recombinant methodology. If the peptide molecule is to be produced chemically, then the methionine residue can be omitted.

FIG. 2 provides the final SAP DNA sequence (SEQ ID NO:13). Flanking nucleotides were added to the DNA sequence shown in FIG. 1 to facilitate cloning. A 5' Nde I site is underlined, as are the 3' Bam HI and internal Sma I sites.

DETAILED DESCRIPTION OF THE INVENTION

Figure 3:
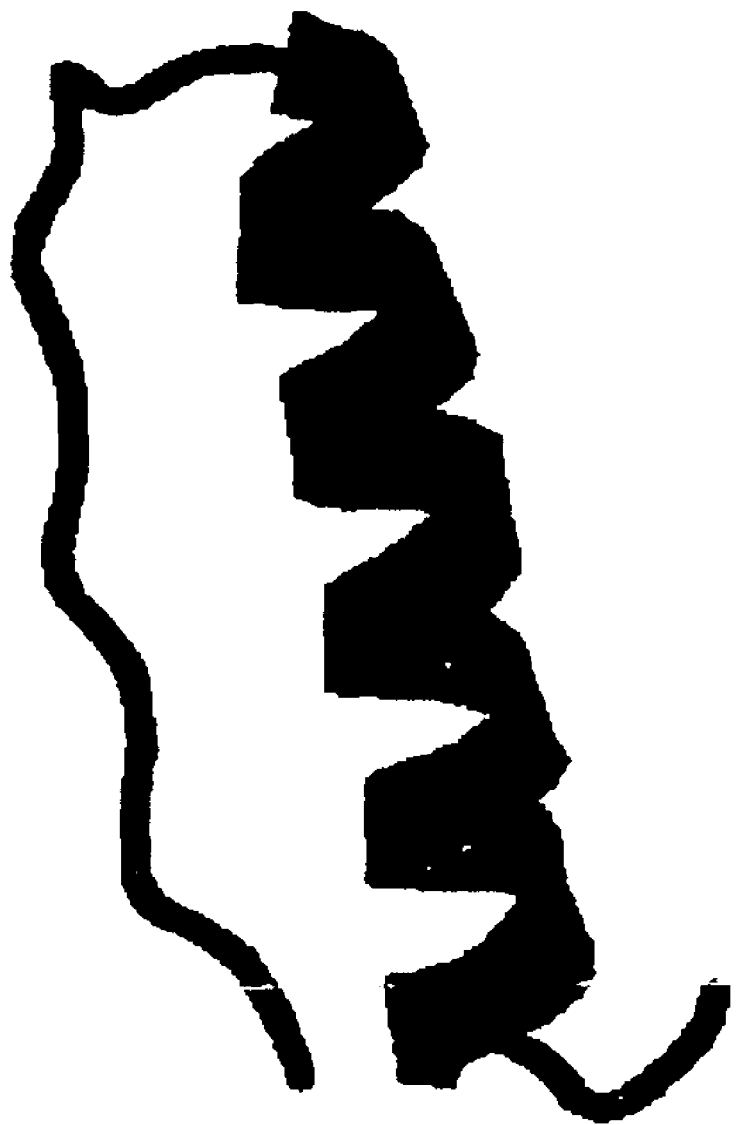
FIG. 3 provides a ribbon diagram of the SAP peptide. The terminal methionine begins the chain on the left and the sequence proceeds into the polyproline helix, into the short loop domain, and finally into the alpha helical region on the right. The peptide ends with the terminal cysteine.
Figure 4:
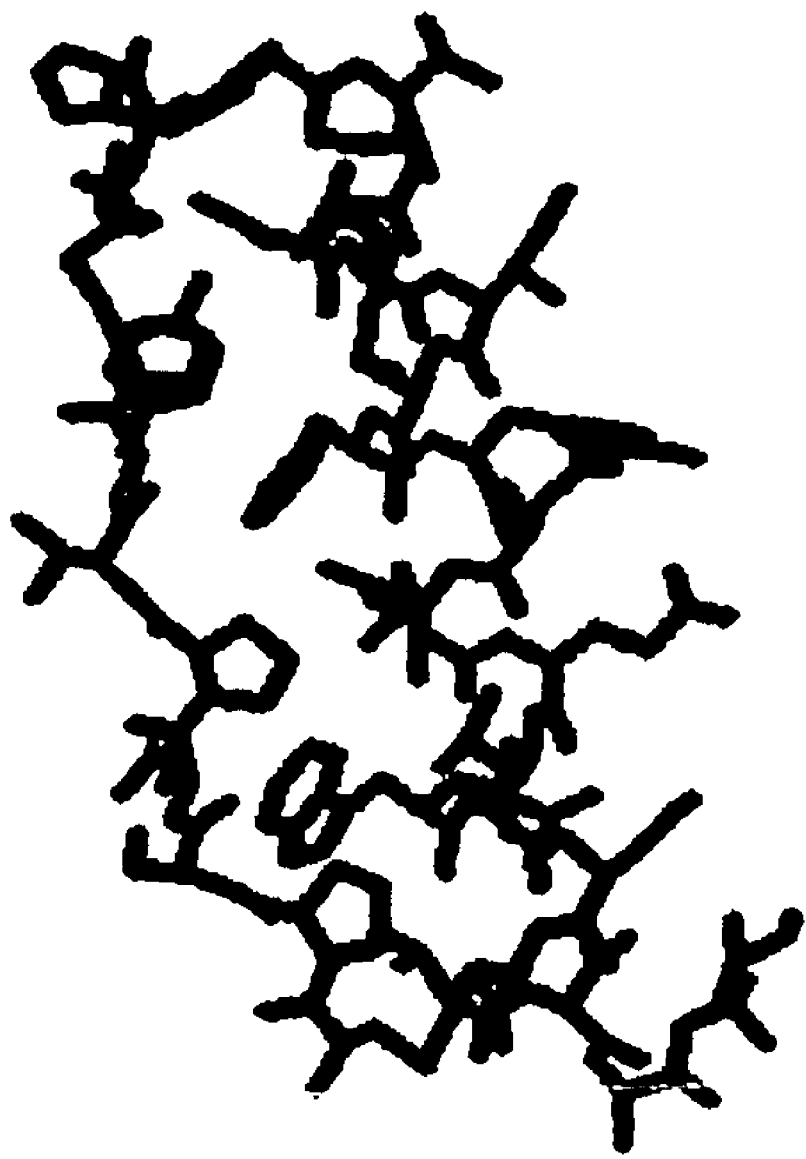
FIG. 4 provides a molecular structure of the SAP peptide from the same view as FIG. 3, but with the amino acid side chains shown.
Figure 5:
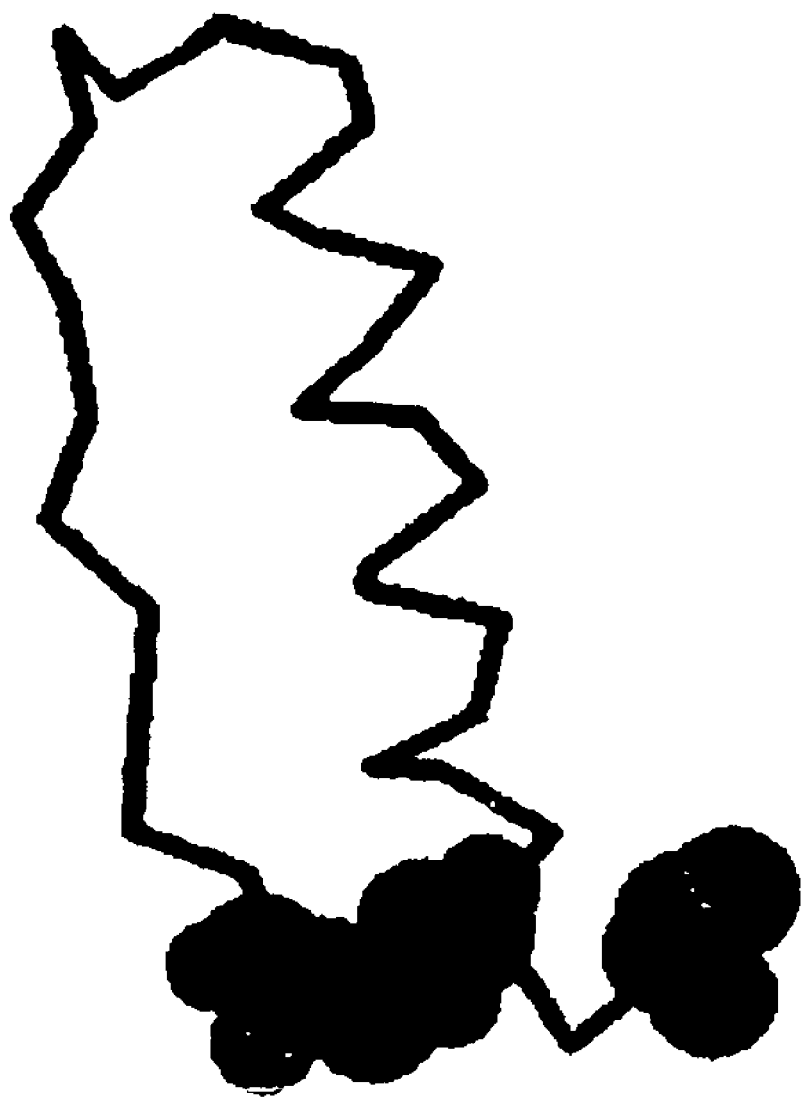
FIG. 5 highlights the positions of the three cysteine residues in the SAP molecule. A disulfide bond can form that nearly cyclizes the SAP peptide. The terminal cysteine is useful for anchoring the peptide to a solid substrate in a diagnostic device.

The invention provides stable peptide backbones into which one or more interactive domains may be incorporated. Such interactive domains may be specific binding domains, inhibitor domains, linkers, labels, solid supports, reactive sites, catalytic sites, useful chemical entities, and reagents. Attachment or incorporation of an interactive domain into the peptide backbone generates a peptide-based reagent.

The invention also provides methods for generating libraries of peptides that can be used as interactive domains. The libraries can range from fully random and totally represented, to targeted and partially represented, and to highly targeted and minimally represented.

Definitions

The term "amino acid sequence" refers to the positional arrangement and identity of amino acids in a peptide, polypeptide or protein molecule. Use of the term "amino acid sequence" is not meant to limit the amino acid sequence to the complete, native amino acid sequence of a peptide, polypeptide or protein.

"Chimeric" is used to indicate that a nucleic acid, such as a vector or a gene, is comprised of more than one nucleic acid segment and that at least two nucleic acid segments are of distinct origin. Such nucleic acid segments are fused together by recombinant techniques resulting in a nucleic acid sequence, which does not occur naturally.

The term "coding region" refers to the nucleotide sequence that codes for a peptide, polypeptide or protein of interest. The coding region of a protein is bounded on the 5' side by the nucleotide triplet "ATG" that encodes the initiator methionine and on the 3' side by one of the three triplets that specify stop codons (i.e., TAA, TAG, TGA).

"Constitutive expression" refers to expression using a constitutive promoter.

"Constitutive promoter" refers to a promoter that is able to express the gene that it controls in all, or nearly all, phases of the life cycle of the cell.

"Complementary" or "complementarity" is used to define the degree of base-pairing or hybridization between nucleic acids. For example, as is known to one of skill in the art, adenine (A) can form hydrogen bonds or base pair with thymine (T) and guanine (G) can form hydrogen bonds or base pair with cytosine (C). Hence, A is complementary to T and G is complementary to C. Complementarity may be complete when all bases in a double-stranded nucleic acid are base paired. Alternatively, complementarity may be "partial," in which only some of the bases in a nucleic acid are matched according to the base pairing rules. The degree of complementarity between nucleic acid strands has an effect on the efficiency and strength of hybridization between nucleic acid strands.

The "derivative" of a reference nucleic acid, protein, polypeptide or peptide, is a nucleic acid, protein, polypeptide or peptide, respectively, with a related but different sequence or chemical structure than the respective reference nucleic acid, protein, polypeptide or peptide. A derivative nucleic acid, protein, polypeptide or peptide is generally made purposefully to enhance or incorporate some chemical, physical or functional property that is absent or only weakly present in the reference nucleic acid, protein, polypeptide or peptide. A derivative nucleic acid differs in nucleotide sequence from a reference nucleic acid whereas a derivative protein, polypeptide or peptide differs in amino acid sequence from the reference protein, polypeptide or peptide, respectively. Such sequence differences include one or more substitutions, insertions, additions, deletions, fusions and truncations, which can be present in any combination. Differences can be minor (e.g., a difference of one nucleotide or amino acid) or more substantial. However, the sequence of the derivative is not so different from the reference that one of skill in the art would not recognize that the derivative and reference are related in structure and/or function. Generally, differences are limited so that the reference and the derivative are closely similar overall and, in many regions, identical. A "variant" differs from a "derivative" nucleic acid, protein, polypeptide or peptide in that the variant can have silent structural differences that do not significantly change the chemical, physical or functional properties of the reference nucleic acid, protein, polypeptide or peptide. In contrast, the differences between the reference and derivative nucleic acid, protein, polypeptide or peptide are intentional changes made to improve one or more chemical, physical or functional properties of the reference nucleic acid, protein, polypeptide or peptide.

"Expression" refers to the transcription and/or translation of an endogenous or exogenous nucleic acid in an organism. Expression generally refers to the transcription and stable accumulation of mRNA. Expression may also refer to the production of protein.

"Expression cassette" means a nucleic acid sequence capable of directing expression of a particular nucleotide sequence. Expression cassettes generally comprise a promoter operably linked to the nucleotide sequence to be expressed (e.g., a coding region) that is operably linked to termination signals. Expression cassettes also typically comprise sequences required for proper translation of the nucleotide sequence. The expression cassette comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term "homology" refers to a degree of similarity between a nucleic acid and a reference nucleic acid or between a polypeptide and a reference polypeptide. Such homology may be partial or complete. Complete homology indicates that the nucleic acid or amino acid sequences are identical. A partially homologous nucleic acid or amino acid sequence is one that is not identical to the reference nucleic acid or amino acid sequence. Hence, a partially homologous nucleic acid has one or more nucleotide differences in its sequence relative to the nucleic acid to which it is being compared. The degree of homology can be determined by sequence comparison. Alternatively, as is understood by those skilled in the art, DNA-DNA or DNA-RNA hybridization, under various hybridization conditions, can provide an estimate of the degree of homology between nucleic acids, (see, e.g., Haines and Higgins (eds.), Nucleic Acid Hybridization, IRL Press, Oxford, U.K.).

"Hybridization" refers to the process of annealing complementary nucleic acid strands by forming hydrogen bonds between nucleotide bases on the complementary nucleic acid strands. Hybridization, and the strength of the association between the nucleic acids, is impacted by such factors as the degree of complementary between the hybridizing nucleic acids, the stringency of the conditions involved, the $T_m$ of the formed hybrid, and the G:C ratio within the nucleic acids.

"Inducible promoter" refers to a regulated promoter that can be turned on in one or more cell types by an external stimulus, such as a chemical, light, hormone, stress, temperature or a pathogen.

An "initiation site" is region surrounding the position of the first nucleotide that is part of the transcribed sequence, which is defined as position +1. All nucleotide positions of the gene are numbered by reference to the first nucleotide of the transcribed sequence, which resides within the initiation site. Downstream sequences (i.e., sequences in the 3' direction) are denominated positive, while upstream sequences (i.e., sequences in the 5' direction) are denominated negative.

An "isolated" or "purified" nucleic acid or an "isolated" or "purified" polypeptide is a nucleic acid or polypeptide that, by the hand of man, exists apart from its native environment and is therefore not a product of nature. An isolated nucleic acid or polypeptide may exist in a purified form or may exist in a non-native environment such as, for example, a transgenic host cell.

The term "label" refers to any atom or molecule that can be used to provide a detectable (preferably quantifiable) signal, and that can be attached to a nucleic acid, peptide or protein. Labels may provide signals detectable by fluorescence, radioactivity, colorimetry, gravimetry, X-ray diffraction or absorption, magnetism, enzymatic activity, and the like.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably linked" means joined as part of the same nucleic acid molecule, so that the function of one is affected by the other. In general, "operably linked" also means that two or more nucleic acids are suitably positioned and oriented so that they can function together. Nucleic acids are often operably linked to permit transcription of a coding region to be initiated from the promoter. For example, a regulatory sequence is said to be "operably linked to" or "associated with" a nucleic acid sequence that codes for an RNA or a polypeptide if the two sequences are situated such that the regulatory sequence affects expression of the RNA or of the coding region (i.e., that the coding sequence or functional RNA is under the transcriptional control of the promoter).

"Promoter" refers to a nucleotide sequence, usually upstream (5') to a coding region, which controls the expression of the coding region by providing the recognition site for RNA polymerase and other factors required for proper transcription. "Promoter" includes but is not limited a minimal promoter that is a short DNA sequence comprised of a TATA-box. Hence, a promoter includes other sequences that serve to specify the site of transcription initiation and control or regulate expression, for example, enhancers. Accordingly, an "enhancer" is a segment of DNA that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Promoters may be derived in their entirety from a native gene, or be composed of different elements derived from different promoters found in nature, or even be comprised of synthetic DNA segments. A promoter may also contain DNA segments that are involved in the binding of protein factors that control the effectiveness of transcription initiation in response to physiological or developmental conditions.

The terms "protein," "peptide" and "polypeptide" are used interchangeably herein.

"Regulatory sequences" and "regulatory elements" refer to nucleotide sequences that control some aspect of the expression of nucleic acid sequences. Such sequences or elements can be located upstream (5' non-coding sequences), within, or downstream (3' non-coding sequences) of a coding sequence. "Regulatory sequences" and "regulatory elements" influence the transcription, RNA processing or stability, or translation of the associated coding sequence. Regulatory sequences include enhancers, introns, promoters, polyadenylation signal sequences, splicing signals, termination signals, and translation leader sequences. They include natural and synthetic sequences.

As used herein, the term "selectable marker" refers to a gene that encodes an observable or selectable trait that is expressed and can be detected in an organism having that gene. Selectable markers are often linked to a nucleic acid of interest that may not encode an observable trait, in order to trace or select the presence of the nucleic acid of interest. Any selectable marker known to one of skill in the art can be used with the nucleic acids of the invention. Some selectable markers allow the host to survive under circumstances where, without the marker, the host would otherwise die. Examples of selectable markers include antibiotic resistance, for example, tetracycline or ampicillin resistance.

As used herein the term "stringency" is used to define the conditions of temperature, ionic strength, and the presence of other compounds such as organic solvents, under which nucleic acid hybridizations are conducted. With "high stringency" conditions, nucleic acid base pairing will occur only between nucleic acids that have a high frequency of complementary base sequences. With "weak" or "low" stringency conditions nucleic acids the frequency of complementary sequences is usually less, so that nucleic acids with differing sequences can be detected and/or isolated.

The terms "substantially similar" and "substantially homologous" refer to nucleotide and amino acid sequences that represent functional equivalents of the instant inventive sequences. For example, altered nucleotide sequences that simply reflect the degeneracy of the genetic code but nonetheless encode amino acid sequences that are identical to the inventive amino acid sequences are substantially similar to the inventive sequences. In addition, amino acid sequences that are substantially similar to the instant sequences are those wherein overall amino acid identity is sufficient to provide a stable peptide backbone. For example, amino acid sequences that are substantially similar to the sequences of the invention are those wherein the overall amino acid identity is 80% or greater, preferably 90% or greater, such as 91%, 92%, 93%, or 94%, and more preferably 95% or greater, such as 96%, 97%, 98%, or 99% relative to the amino acid sequences of the invention.

The "variant" of a reference nucleic acid, protein, polypeptide or peptide, is a nucleic acid, protein, polypeptide or peptide, respectively, with a related but different sequence than the respective reference nucleic acid, protein, polypeptide or peptide. The differences between variant and reference nucleic acids, proteins, polypeptides or peptides are silent or conservative differences. A variant nucleic acid differs in nucleotide sequence from a reference nucleic acid whereas a variant nucleic acid, protein, polypeptide or peptide differs in amino acid sequence from the reference protein, polypeptide or peptide, respectively. A variant and reference nucleic acid, protein, polypeptide or peptide may differ in sequence by one or more substitutions, insertions, additions, deletions, fusions and truncations, which may be present in any combination. Differences can be minor (e.g., a difference of one nucleotide or amino acid) or more substantial. However, the structure and function of the variant is not so different from the reference that one of skill in the art would not recognize that the variant and reference are related in structure and/or function. Generally, differences are limited so that the reference and the variant are closely similar overall and, in many regions, identical.

The term "vector" is used to refer to a nucleic acid that can transfer another nucleic acid segment(s) into a cell. A "vector" includes, inter alia, any plasmid, cosmid, phage or nucleic acid in double- or single-stranded, linear or circular form that may or may not be self-transmissible or mobilizable. It can transform prokaryotic or eukaryotic host cells either by integration into the cellular genome or by existing extrachromosomally (e.g., autonomous replicating plasmid with an origin of replication). Vectors used in bacterial systems often contain an origin of replication that allows the vector to replicate independently of the bacterial chromosome. The term "expression vector" refers to a vector containing an expression cassette.

The term "wild-type" refers to a gene or gene product that has the characteristics of that gene or gene product when isolated from a naturally occurring source. A wild-type gene is the gene form most frequently observed in a population and thus arbitrarily is designed the "normal" or "wild-type" form of the gene. In contrast, the term "variant" or "derivative" refers to a gene or gene product that displays modifications in sequence and or functional properties (i.e., altered characteristics) when compared to the wild-type gene or gene product. Naturally-occurring derivatives can be isolated. They are identified by the fact that they have altered characteristics when compared to the wild-type gene or gene product.

Peptide Backbones

The peptide backbones of the invention have sequences that are related to a small, stable peptide called Avian Pancreatic Polypeptide. APP is a pancreatic hormone that binds to its receptor via its N- and C-termini (Gehlert et al., 1996; Gingerich et al., 1991; Fuhlendorf et al., 1990). APP has thirty six amino acids and forms a peptide with an unusual primary structure (Hazelwood, 1990, reviewed by Cerda-Reverter and Larhammar, 2000). Normally, a peptide with thirty six amino acids is too short to provide enough packing energy to stabilize a unique conformation. However, the APP peptide is remarkably stable due to a combination of secondary and tertiary interactions (Bjornholm and Jorgensen, 1993; Kruger et al., 1985). The peptide begins with an extended polyproline helix, followed by a short loop region, a long alpha helix, and terminates in a short disordered chain. The juxtaposition of the polyproline helix and the alpha helix results in significant van der Waals and hydrophobic interactions in the interhelical contact region (Blundell et al., 1981). Such interactions stabilize the folded peptide structure. APP has served as a model system for investigators who are interested in molecular dynamics simulations and protein fold prediction (see, e.g., Alexander and MacKerell, 1991).

The sequence of wild-type APP is as follows SEQ ID NO:1):
GPSQPTYPGD DAPVEDLIRF YDNLQQYLNV VTRHRY In contrast to the APP sequence, the peptide backbones of the invention are modified in order to engineer a molecule that is more useful for diagnostic applications. Residues altered to form one example of a peptide backbone of the invention are shown in bold within SEQ ID NO:1 above. In one embodiment, Tyr27 was substituted with Trp (SEQ ID NO:2, GPSQPTYPGD DAPVEDLIRF YDNLQQWLNV VTRHRY). This amino acid substitution improves packing within the hydrophobic core and also provides a useful intrinsic spectroscopic probe. In another embodiment, Gly1 was changed to Met-Cys (SEQ ID NO:3, MCPSQPTYPGD DAPVEDLIRF YDNLQQYLNV VTRHRY) This alteration allows the molecule to be produced using recombinant methodology, where an initiating Met is required for transcription and translation in E. coli. In another embodiment, a Cysteine residue is added at position 30 (replacing Val30) to form a stabilizing disulfide bond with the Cysteine added at the N-terminus (SEQ ID NO:4, MCPSQPTYPGD DAPVEDLIRF YDNLQQYLNC VTRHRY). In another embodiment, Asp11 was replaced with Pro in order to form a more stable kink to the interhelical loop domain and as a way of introducing a unique Sma I site into a nucleic acid encoding the peptide backbone (SEQ ID NO:5, GPSQPTYPGD PAPVEDLIRF YDNLQQYLNV VTRHRY). Similarly Ala12 can be altered to Gly in order to provide a Sma I site in a nucleic acid encoding the peptide backbone (SEQ ID NO:6, GPSQPTYPGD DGPVEDLIRF YDNLQQYLNV VTRHRY). The sequence RHRY (SEQ ID NO:7) can be removed from SEQ ID NO:1, as this sequence has been implicated in APP receptor binding. After removal of RHRY (SEQ ID NO:7), two alanine residues can be added in order to properly space and orient the terminal cysteine residue (SEQ ID NO:8, GPSQPTYPGD DAPVEDLIRF YDNLQQYLNV VTAA). A C-terminal Cys can be added to sequester and properly orient the peptide backbone onto gold or another solid support or surface that forms part of a diagnostic device (SEQ ID NO:9, GPSQPTYPGD DAPVEDLIRF YDNLQQYLNV VTRHRYC; or (SEQ ID NO:10, GPSQPTYPGD DAPVEDLIRF YDNLQQYLNV VTC).

Such sequence changes have been used to generate a 35 amino acid peptide backbone with amino acid sequence SEQ ID NO:11 (MCPSQPTYPGD PGPVEDLIRFYDNLQQWLNCVTAAC). In another embodiment of the invention, the peptide backbone does not have the initial methionine. Instead, the peptide has SEQ ID NO:14 (CPSQPTYPGD PGPVEDLIRF YDNLQQWLNC VTAAC).

Nucleotide sequence SEQ ID NO:12 is one example of a nucleic acid that can encode SEQ ID NO:11.

```
M   C   P   S   Q   P   T   Y   P   G   D   P
ATG TGC CCG AGC CAG CCG ACC TAT CCG GGC GAT CCC

G   P   V   E   D   L   I   R   F   Y   D   N
GGG CCG GTG GAA GAT CTG ATC CGC TTT TAT GAT AAC

L   Q   Q   W   L   N   C   V   T   A   A   C
CTG CAG CAG TGG CTG AAC TGC GTG ACC GCC GCC TGC

*
TAG
```

Nucleotide sequence SEQ ID NO:13 is another example of a nucleic acid that can encode SEQ ID NO:11.

```
1              11             21             31
ACACACCATA     TGTGCCCGAG     CCAGCCGACC     TATCCGGGCG
TGTGTGGTAT     ACACGGGCTC     GGTCGGCTGG     ATAGGCCCGC 41             51             61             71
ATCCCGGGCC     GGTGGAAGAT     CTGATCCGCT     TTTATGATAA
TAGGGCCCGG     CCACCTTCTA     GACTAGGCGA     AAATACTATT
```

```
-continued
81          91          101         111
CCTGCAGCAG  TGGCTGAACT  GCGTGACCGC  CGCCTGCTAG
GGACGTCGTC  ACCGACTTGA  CGCACTGGCG  GCGGACGATC 121         131
GGATCCACAC  AC
CCTAGGTGTG  TG
```

An alignment of wild-type APP (SEQ ID NO:1) with the SEQ ID NO:14 peptide backbone of the invention is provided below.

```
                                              SEQ ID NO:1
GPSQPTYPGD DAPVEDLIRF YDNLQQYLNV VTRHRY:

SEQ ID NO:14
CPSQPTYPGD PGPVEDLIRF YDNLQQWLNC VTAAC:
```

Insertions can be made in peptide backbones having any one of SEQ ID NO:2–6 or SEQ ID NO:8–11 or SEQ ID NO:14. One convenient location for such insertions is between residues Proline-11 and Glycine-12, found near the center of the loop region. If a nucleic acid having SEQ ID NO:12 is used to generate peptide-based reagents with insertions between residues Proline-11 and Glycine-12, insertions should be inserted between nucleotides 36 and 37 of SEQ ID NO:12.

Many of the amino acids shared by SEQ ID NO:1 and SEQ ID NO:2–6, 8–11 or 14 make important intramolecular contacts within the peptide and play a role in maintaining stability and conformation in the peptide. However, some variability in backbone sequence will not adversely affect the stability of the peptide backbone. Accordingly, the invention is also directed to variants and derivatives of the peptide backbones of the invention, for example, variants and derivatives of SEQ ID NO:2–6, 8–11 or 14.

Derivative and variant peptide backbones of the invention are derived from the reference peptide backbones by deletion or addition of one or more amino acids to the N-terminal and/or C-terminal end of the reference peptide backbones; deletion or addition of one or more amino acids at one or more sites within the reference peptide backbones; or substitution of one or more amino acids at one or more sites within the reference peptide backbones. Thus, the peptides backbones of the invention may be altered in various ways including amino acid substitutions, deletions, truncations, and insertions.

Such variant and derivative peptides may result, for example, from human manipulation. Methods for such manipulations are generally known in the art. For example, amino acid sequence variants of the peptides can be prepared by mutations in the DNA. Methods for mutagenesis and nucleotide sequence alterations are well known in the art. See, for example, Kunkel, Proc. Natl. Acad. Sci. USA, 82, 488 (1985); Kunkel et al., Methods in Enzymol., 154, 367 (1987); U.S. Pat. No. 4,873,192; Walker and Gaastra, eds., Techniques in Molecular Biology, MacMillan Publishing Company, New York (1983) and the references cited therein. Guidance as to appropriate amino acid substitutions that do not adversely affect the structural integrity and/or biological activity of the peptide of interest may be found in the model of Dayhoff et al., Atlas of Protein Sequence and Structure, Natl. Biomed. Res. Found., Washington, D.C. (1978), herein incorporated by reference.

Portions of the derivatives and variants of the peptide backbones of the invention have identity with at least about 90%, 91%, 92%, 93% or 94% of the amino acid positions of any one of SEQ ID NO:2–6, 8–11 or 14 and such portions generally have a stability and an overall three-dimensional structure similar to that peptide backbones having any one of SEQ ID NO:2–6, 8–11 or 14. In a desirable embodiment, portions of the peptide derivatives and variants have identity with at least about 95% or 96% of the amino acid positions of any one of SEQ ID NO:2–6, 8–11 or 14 and those portions generally have a stability and an overall three-dimensional structure similar to that peptide backbones having SEQ ID NO:2–6, 8–11 or 14. In a more desirable embodiment, portions of the peptide derivatives and variants have identity with at least about 97% or 98% of the amino acid positions of any one of SEQ ID NO:2–6, 8–11 or 14 and those portions generally have a stability and an overall three-dimensional structure similar to that peptide backbones having SEQ ID NO:2–6, 8–11 or 14.

Amino acid residues of the peptide backbones and of the derivatives and variants of the peptide backbones can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | Bala |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | Harg |

TABLE 1-continued

| Amino Acid | One-Letter Symbol | Common Abbreviation |
| --- | --- | --- |
| N-acetyl lysine | | AcLys |
| 2,4-Diamino butyric acid | | Dbu |
| p-Aminophenylalanine | | Phe(pNH$_2$) |
| N-methylvaline | | MeVal |
| Homocysteine | | Hcys |
| Homoserine | | Hser |
| ε-Amino hexanoic acid | | Aha |
| δ-Amino valeric acid | | Ava |
| 2,3-Diaminobutyric acid | | Dab |

Peptide variants that are encompassed within the scope of the invention can have one or more amino acids substituted with an amino acid of similar chemical and/or physical properties, so long as the backbone portions of these variant peptides retain a stability and an overall three-dimensional structure similar to that of peptide backbones having any one of SEQ ID NO:2–6, 8–11, or 14. Derivative peptide backbones can have additional peptide or chemical moieties as well as one or more amino acids substituted with amino acids having different chemical and/or physical properties, so long as these derivative peptide backbones have a stability and an overall three-dimensional structure similar to that of peptide backbones having any one of SEQ ID NO:2–6, 8–11 or 14.

Amino acids that are substitutable for each other to form a variant peptide of the invention generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a polypeptide.

Certain commonly encountered amino acids that are not genetically encoded and that can be present, or substituted for an amino acid, in the variant polypeptides of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl));

2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues that may comprise the variant and derivative polypeptides described herein. Other amino acid residues that are useful for making the variant and derivative polypeptides described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
|---|---|---|
| Hydrophobic | F, L, I, V | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | S, K | Cit, hCys |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

Peptide backbones of the invention can have any amino acid substituted by any similarly classified amino acid to create a variant peptide, so long as the peptide variant has a stability and an overall three-dimensional structure similar to that of a peptide backbones having any one of SEQ ID NO:2–6, 8–11 or 14.

While the peptide backbones of the invention can have variable regions, one of skill in the art may also select an invariant backbone structure for a given purpose. Thus, one of skill in the art may utilize an invariant backbone structure to generate a library of peptide-based reagents or a library of peptides. The chemical and physical properties of the invariant backbone structure will then remain constant and any variation in binding, solubility, stability or other biological, chemical or physical property can be attributed to the chemical or peptide moieties attached to the peptide backbones.

The peptide backbones of the invention are comparatively small. This means that a high proportion of the molecular mass of a peptide-based reagent incorporating the peptide backbone is utilized for its intended purpose. Hence, for example, when an antigen recognition site is attached or incorporated into the peptide backbone, a very small peptide-based reagent is generated that mimics the binding properties of a much larger antibody. Such a peptide-based "antibody" reagent is more stable than an antibody, has fewer antigenic epitopes and is easier to engineer and produce.

Interactive Domains

According to the invention, interactive domains can be attached or incorporated into the peptide backbones of the invention, for example, any one of SEQ ID NO:2–6, 8–11 or 14. Such interactive domains can be any molecule or moiety selected by one of skill in the art. Useful interactive domains include, for example, specific binding domains, inhibitor domains, linkers, labels, solid supports, enzymatic active sites, catalytic sites, useful chemical entities and reagents and the like.

Examples of interactive domains provided by the invention also include a peptide encoding a portion of the recognition sequence from Bovine Pancreatic Trypsin Inhibitor (PYRIRF, residues 561 to 566 in the molecule, SEQ ID NO:15) and a peptide identified by the library search program described herein using bovine pancreatic trypsin as the target protein (YKLKY, SEQ ID NO:18). A peptide-based reagent that combines the SEQ ID NO:15 interactive domain with the SEQ ID NO:11 peptide backbone has SEQ ID NO:21 (CPSQPTYPGDPPYRIRFGPVEDLIRFYDNLQ QWLNCVTAAC). A peptide-based reagent that combines the SEQ ID NO:18 interactive domain with the SEQ ID NO:11 peptide backbone has SEQ ID NO:22 (CPSQPTYPGDPYKLKY GPVEDLIRFYDNLQQWLNCVTAAC).

Libraries of peptides may be generated to provide a multitude of interactive domains. For example, libraries of peptides can be generated to act as inhibitors, binding agents, ligands for receptors and antigen recognition sites. In one embodiment, the peptides are designed to interact with a target protein, nucleic acid or antigen. Specific sites or sequences within the target protein, nucleic acid or antigen can be targeted for interaction with the peptides provided by the libraries. Peptides identified as having the appropriate properties can then be incorporated into or attached onto the peptide backbones of the invention.

In general, an input or target protein or nucleic acid is selected for interaction with the peptides of the library. One of skill in the art can select any target protein or nucleic acid of interest. For example, the target protein can be an antigen, an antibody, an enzyme, a hormone, a receptor, a ligand, a DNA-binding protein, a membrane-associated protein, or any structural protein. Examples of input or target nucleic acid sites to which the peptides of the library can bind include promoters, enhancers, polyadenylation sites, introns, splicing signals, termination signals, and translation leader sequences.

A search zone on the input or target protein or nucleic acid is defined. Such a search zone defines the physical and chemical properties of the site to which the peptide will interact or bind. For example, the search zone can contain the x, y and z coordinates of all nonhydrogen atoms in the peptide-interaction site of the protein or the nucleic acid. Other parameters that may be considered in defining the search zone include the charge, hydrophilicity, hydrophobicity, distance and orientation of atoms within the input or target protein or nucleic acid.

One of skill in the art can choose the length of the library peptides. For example, desirable peptides in the library can be about 1 to about 30 amino acids in length. More desirable peptides in the library can be about 1 to about 25 amino acids in length. Even more desirable peptides in the library can be about 1 to about 20 amino acids in length. Even more desirable peptides in the library can be about 2 to about 15 amino acids in length. Even more desirable peptides in the library can be about 2 to about 10 amino acids in length. Especially desirable peptides in the library can be about 2 to about 8 amino acids in length.

In one embodiment, the peptide length was about one to six amino acids in length. Initial modeling studies, including long range molecular dynamics simulations, indicate that up to six amino acid residues can be inserted into the center of the loop portion without negatively impacting the stability of the molecule. These six amino acids could encode an interactive domain having binding affinity and specificity for a target protein or nucleic acid.

One of skill in the art can select how many amino acid substitutions can occur at each position of the peptides within the library. Similarly, the user can select any combination of amino acids to place at a given position within the peptides of the library. For example, the skilled artisan can select any class or type of amino acid to be placed at a given position. Such a class of amino acids can, for example, be a class of genetically encoded L-amino acids, naturally occurring non-genetically encoded L-amino acids, synthetic L-amino acids, D-enantiomers of genetically encoded amino acids, D-enantiomers of naturally occurring non-genetically encoded amino acids, or synthetic D-amino acids. Other classes of amino acids include hydrophilic amino acids, hydrophobic amino acids, cysteine-like amino acids, acidic amino acids, basic amino acids, polar amino acids, aromatic amino acids, apolar amino acids or aliphatic amino acids. Further examples of types and classes amino acids are provided hereinabove.

The selected peptide library file is then used as input to a docking program that fits each peptide to the search zone on the target protein or nucleic acid. Some docking programs are available, for example, the Molecular Simulations Inc (MSI) program LigandFit™. The docking program provides a fit score for each peptide type. The output file can be rank ordered by peptide fit score. Top scoring peptides are potentially the best suited to interact with the input target protein or nucleic acid.

Figure 13:
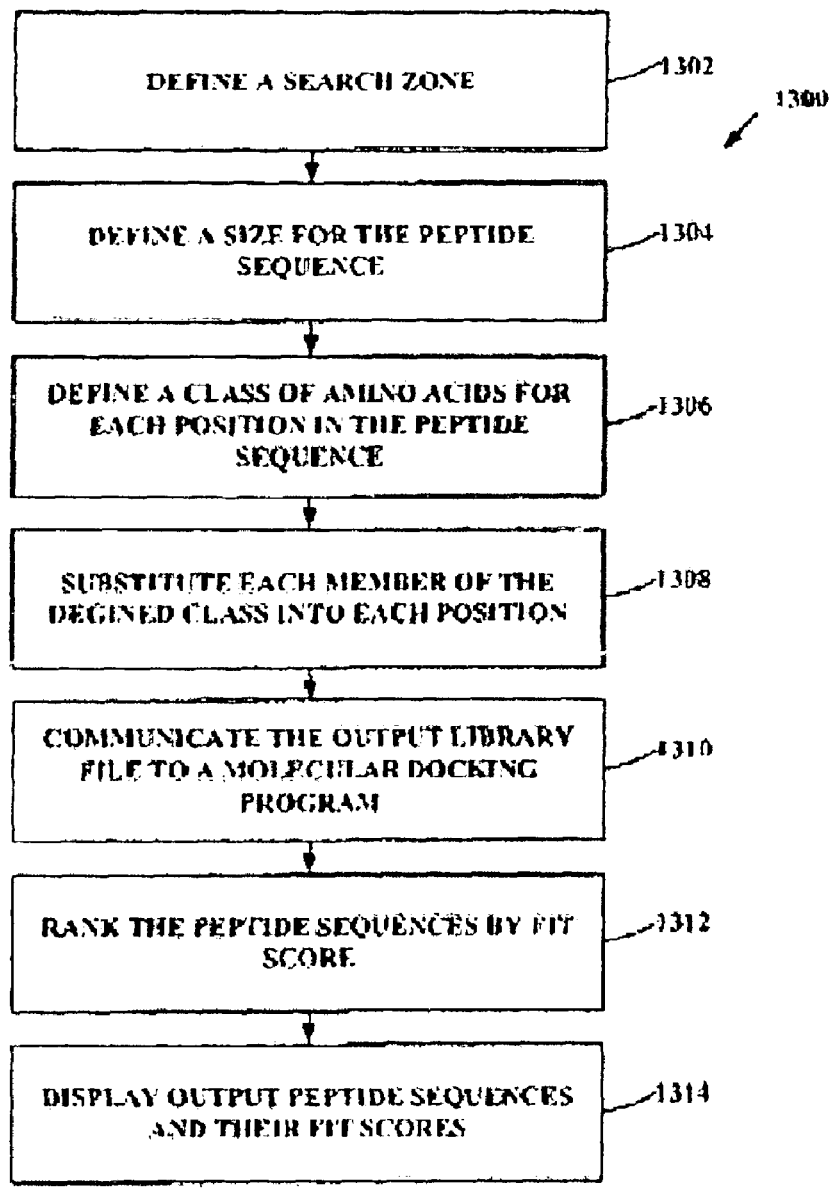
FIG. 13 is a flow chart of a method embodiment of the present invention.

In one embodiment, the method includes the several steps that are outlined in FIG. 13. One step is to define a search zone 1302. Such a search zone is the chosen site of interaction on a target protein to which a peptide can interact. The interactive peptide domains of the invention can interact with the search zone. Search zones can be, for example, a binding site, an antigen recognition site, an active site, an inhibitor binding site and the like.

Another step that can be included in the method is to define a size for the peptide 1304. As described herein, peptides can be a variety if lengths. For example, peptides can be about 1 to about 30 amino acids in length.

An additional step that may be included in the method is to define a class of amino acids for each position in the amino acid sequence of the peptide 1306. As provided herein, one of skill in the art each position of the amino acid sequence of the peptide can have distinct chemical and physical properties. Hence, amino acids having related physical structures, or having specified chemical properties, or having specified solubility properties can form the class.

In another step, each member of the class of amino acids can be iteratively substituted or placed into the prescribed position of the peptide to generate an output library file 1308. Such an output library file contains a plurality of output peptide sequences, each with a distinct peptide sequence.

An additional step that can be included in the method is to communicate the output library file to a molecular docking program 1310. The molecular docking program can fit each of the plurality of output peptide sequences to the search zone and then to create a target protein-peptide sequence fit score. Such a target protein-peptide sequence fit score is a measure of how well a given peptide will interact with, bind to or fit within the search zone. Peptides having a high target protein-peptide sequence fit score will generally interact, bind or fit well with the chosen site in the target protein or target nucleic acid.

In another step of the method, the plurality of output peptides sequences can be ranked by target protein-peptide sequence fit score 1312. Such a ranking permits ready assessment of which peptide(s) will most effectively interact, bind or fit the chosen site in the target protein or target nucleic acid.

An additional step that can be included in the method is to display each of the plurality of output peptide sequences and its associated target protein-peptide sequence fit score 1314. At least a portion of the plurality of output peptide sequences can stably interact with the target protein. Accordingly, one of skill in the art may choose to list all output peptide sequences.

Alternatively, rather than listing all possible peptide sequences with their associated fit scores, only a percentage of the top-scoring peptides can be displayed when that percentage is inputted. Alternatively, the program may randomly pick a certain percentage of all the possible peptides to write out to the final structure file. Selection of such a percentage can limit the size of the output library file size and/or the library complexity.

Figure 14:
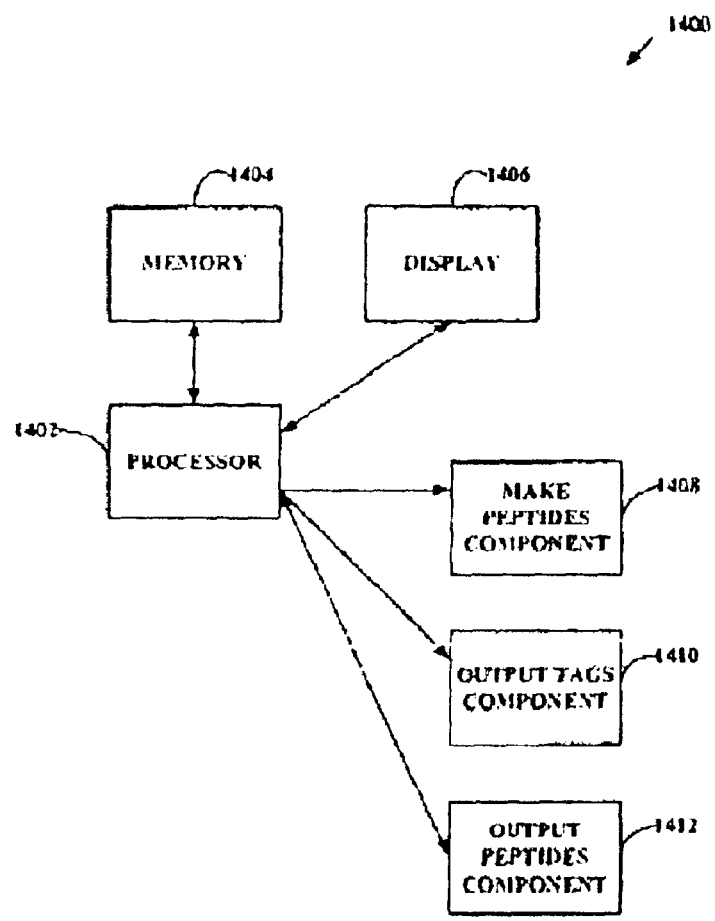
FIG. 14 is a block diagram of an embodiment of the present invention as a system for creating peptides.

In another embodiment, the invention provides a system for creating peptide sequences (see FIG. 14). Such a system can include a processor 1402. A memory 1404 and/or a display 1406 can be coupled to the processor. The system can also include a make peptide sequence component 1408 capable of executing on the processor to generate peptide sequences. The output tags or class component 1410 is capable of executing on the processor to display each class of amino acid residues used by the make peptide sequence component. The system can also include an output peptide sequence component 1412 capable of executing on the processor to display peptide sequences.

A processor, such as a microprocessor in a Personal Computer (PC) is the logic circuitry that responds to and processes the basic instructions that drive a computing device. Computing devices include PCs, laptops, general purpose computers, and the like. A memory is the electronic holding place for instructions and data accessible to a computing device. During normal operation, memory usually contains an operating system, application programs, and data. Kinds of memory include random access memory (RAM), read-only memory (ROM), programmable memory (PROM), and erasable programmable ROM (EPROM) as well as storage devices such as hard drives and floppy disks. A display is a computer output mechanism that shows text and often graphic images to the computer user. Examples of displays include printers, monitors, and the like.

In one embodiment, the output class component is capable of displaying each class of amino acid residues used by the make peptide sequence component.

In another embodiment, the invention provides a machine-accessible medium having associated content capable of directing the machine to perform a method. The method can be one of the methods described above.

Figure 15:
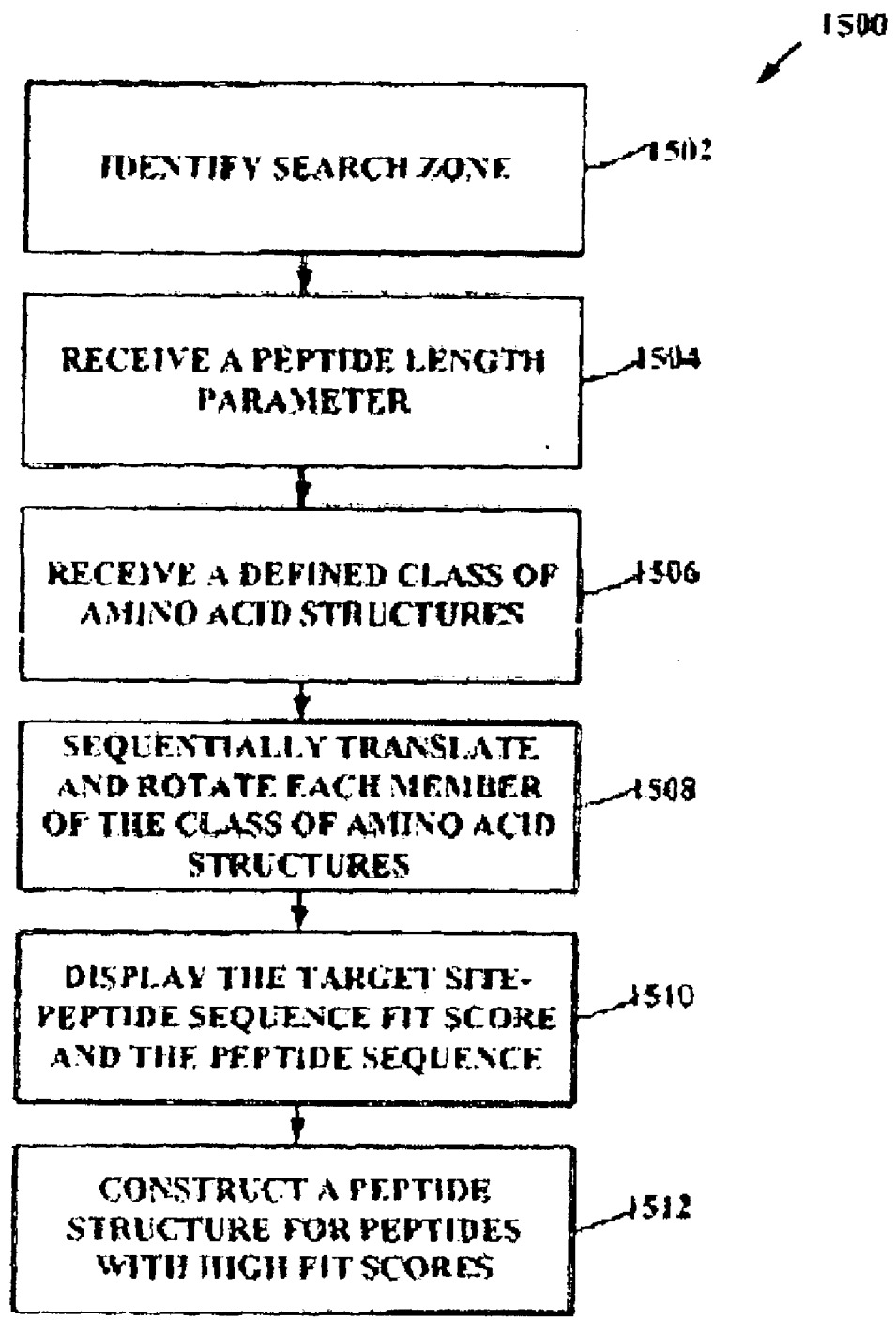
FIG. 15 is a flow chart of another method embodiment of the present invention.

The method performed on the machine-accessible medium can also be the method illustrated in FIG. 15 that includes the following steps. In one step the method involves receiving a search zone 1502. As described above, the search zone can provide a plurality of coordinates for atoms in a target site to which a plurality of peptides can bind with varying affinities.

In another step, the method can include a step of receiving a peptide length parameter 1504. Such a peptide length parameter can be a definition of the number of amino acids to be included in the peptide.

An additional step can be included that involves receiving a defined class of amino acid structures 1506 to be analyzed for fitness at each position along the peptide length. In this step, the user can define what types or classes of amino acids are to be placed into the peptide sequence at prescribed positions.

In another step, the method can include generating a output library file that includes a plurality of output peptide sequences 1508. The output peptide sequences are a collection of peptide sequences containing each amino acid from each defined class of amino acid structures at each position along the peptide length.

An additional step can be included in the method that includes sequentially translating and rotating each member of the class of amino acid structures 1510 at a defined position within a peptide. Such translation and rotation is performed relative to the search zone to sequentially create a peptide sequence with a target site-peptide sequence fit score.

In another step, the method can include ranking peptide sequences by target site-peptide sequence fit scores 1512. As described above, such a ranking permits ready assessment of which peptide(s) will most effectively interact, bind or fit the chosen site in the target protein or target nucleic acid.

An additional step can be included in the method that includes displaying a selected percentage of the target site-peptide sequence fit scores with the associated peptide sequences 1514.

The method can also include constructing a desirable peptide structure using the target site-peptide sequence fit scores and the associated peptide sequences 1516.

An additional step can be included in the method that includes displaying labels for the output peptide sequences and/or storing the search zone.

One example of a peptide interactive domain selected by the library screening program described herein using bovine pancreatic trypsin as the target protein is YKLKY (SEQ ID NO:18). This interactive domain peptide was placed in the SEQ ID NO:11 peptide backbone to generate a peptide having SEQ ID NO:22 (CPSQPTYPGDPYKLKY GPVEDLIRFYDNLQQWLNCVTAAC) (also called SAP-2). This library program-selected peptide bound well to bovine pancreatic trypsin. For comparison, a natural peptide from Bovine Pancreatic Trypsin Inhibitor (PYRIRF, residues 561 to 566 in the molecule, SEQ ID NO:15) was inserted into the SEQ ID NO:11 peptide backbone to generate SEQ ID NO:21 (CPSQPTYPGDPPYRIRFGPVEDLIRFYDNLQQWLN CVTAAC) (also called SAP-1). The library-selected peptide having SEQ ID NO:22 had slightly lower binding affinity for bovine pancreatic trypsin when compared to the naturally-selected peptide having SEQ ID NO:21. However, insertion of either peptide SEQ ID NO:15 or 18 into the SEQ ID NO:11 peptide backbone generated peptide-based reagents that were even more stable than the peptide backbone without insertions. Hence, the methods of the invention can be used to generate very stable peptide-based reagents.

In one embodiment, the peptide interactive domain has antigen-recognition specificity. Such an antigen-recognizing peptide interactive domain can be built into or attached onto the peptide backbone to generate a peptide-based reagent with antigen binding ability. The antigen recognition element that comprises the peptide interactive domain is a short peptide that is inserted into a selected insertion site within the peptide backbone. The insertion site is selected so that the peptide backbone does not lose stability. Stable insertion of such a peptide interactive positively affects the binding specificity and affinity of the antigen-recognizing peptide because of the decrease in configurational entropy of the peptide insert relative to free peptide. One example of an appropriate insertion site within the peptide backbone is within the loop portion of a peptide having any one of SEQ ID NO:2–6, 8–11 or 14. A desirable insertion site is between residues Proline-11 and Glycine-12.

The antigen-recognizing peptide interactive domains of the invention can be identified using the peptide library searching program of the invention or by identifying the antigen binding domain of an existing antibody. Antibodies can also be made by conventional procedures in order to identify useful antigen-binding peptide interactive domains.

The preparation of polyclonal antibodies is well-known to those skilled in the art. See, for example, Green, et al., Production of Polyclonal Antisera, in: *Immunochemical Protocols* (Manson, ed.), pages 1–5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

The preparation of monoclonal antibodies likewise is conventional. See, for example, Kohler & Milstein, Nature, 256:495 (1975); Coligan, et al., sections 2.5.1–2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1–2.7.12 and sections 2.9.1–2.9.3; Barnes, et al., Purification of Immunoglobulin G (IgG), in: *Methods in Molecular Biology*, Vol. 10, pages 79–104 (Humana Press (1992).

Recombinant Expression of Encoding Peptide-Based Reagents

Nucleic acids encoding the peptide backbones, peptide-based reagents and antigen-recognizing peptides of the invention may be used for the recombinant expression of those peptides. Generally, recombinant expression of a nucleic acid encoding a peptide of the invention is effected by introducing the nucleic acid into an expression vector adapted for use in particular type of host cell.

The nucleic acids of the invention can be introduced and expressed in any host organism, for example, in both prokaryotic or eukaryotic host cells. Examples of host cells include bacterial cells, yeast cells, cultured insect cell lines, and cultured mammalian cells lines. Preferably, the recombinant host cell system is selected that processes and post-translationally modifies nascent peptides in a manner desired by one of skill in the art. If post-translational is not critical, any convenient host organism may be selected. For purposes of expressing and isolating many peptide backbones, peptide-based reagents and antigen-recognizing peptides of the invention, prokaryotic organisms are desirable, for example, *Escherichia coli*. Accordingly, the invention provides host cells comprising the expression vectors of the invention.

The nucleic acids to be introduced can be conveniently placed in expression cassettes for expression in an organism of interest. Such expression cassettes will comprise a transcriptional initiation region linked to a nucleic acid of the invention. Expression cassettes preferably also have a plurality of restriction sites for insertion of the nucleic acid to be under the transcriptional regulation of various control elements. The expression cassette additionally may contain selectable marker genes. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Preferably the nucleic acid in the vector is under the control of, and operably linked to, an appropriate promoter or other regulatory elements for transcription in a host cell. The vector may be a bi-functional expression vector that functions in multiple hosts. The transcriptional cassette generally includes in the 5'-3' direction of transcription, a promoter, a transcriptional and translational initiation region, a DNA sequence of interest, and a transcriptional and translational termination region functional in the organism. The termination region may be native with the transcriptional initiation region, may be native with the DNA sequence of interest, or may be derived from another source.

Efficient expression of recombinant nucleic acids in prokaryotic and eukaryotic cells generally requires regulatory control elements directing the efficient termination and polyadenylation of the resulting transcript. Transcription termination signals are generally found downstream of the polyadenylation signal and are a few hundred nucleotides in length. The term "poly A site" or "poly A sequence" as used herein denotes a nucleic acid sequence that directs both the termination and polyadenylation of the nascent RNA transcript. Efficient polyadenylation of the recombinant transcript is desirable as transcripts lacking a poly A tail are unstable and are rapidly degraded.

Nucleic acids encoding peptide backbones, peptide-based reagents and antigen-recognizing peptides of the invention may be introduced into bacterial host cells by a method known to one of skill in the art. For example, such nucleic acids can be introduced into bacterial cells by commonly used transformation procedures such as by treatment with calcium chloride or by electroporation. If the peptide backbones, peptide-based reagents and antigen-recognizing peptides of the invention are to be expressed in eukaryotic host cells, nucleic acids encoding those peptides may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation.

Thus, one aspect of the invention is to provide expression vectors and host cells comprising a nucleic acid encoding peptide backbones, peptide-based reagents and antigen-recognizing peptides of the invention. A wide range of expression vectors are available in the art. Description of various expression vectors and how to use them can be found among other places in U.S. Pat. Nos. 5,604,118; 5,583,023; 5,432,082; 5,266,490; 5,063,158; 4,966,841; 4,806,472; 4,801,537; and Goedel et al., Gene Expression Technology, Methods of Enzymology, Vol. 185, Academic Press, San Diego (1989). Recombinant DNA and molecular cloning techniques that can be used to help make and use aspects of the invention are described by Sambrook et al., Molecular Cloning: A Laboratory Manual Vol. 1–3, Cold Spring Harbor laboratory, Cold Spring Harbor, N.Y. (2001); Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

Diagnostic and Therapeutic Methods

The peptide-based reagents of the invention can serve as the basis for a therapeutic method or a diagnostic method or device. The present peptide-based reagents that have antigen-recognizing interactive domains can substitute for antibodies. Peptide-based reagents that have enzymatic catalytic sites or enzymatic active sites as their interactive domains can substitute for enzymes. Peptide-based reagents that have inhibitors as their interactive domain can be used in place of inhibitors. Accordingly, the utility of peptide-based reagents provided by the invention is very broad.

In particular, such peptide-based reagents can be used in any procedure known to one of skill in the art for detecting a target nucleic acid or protein of interest. For example, the peptide-based reagents of the invention can be used in any molecular biology detection procedure, including any enzymatic assays, inhibition assays or immunoassays. Biophysical detection procedures can be coupled with such procedures, or used separately as dictated by one of skill in the art. Such procedures include, for example, procedures such as surface plasmon resonance, fluorescence, lateral flow procedures. These procedures produce a robust and useful means of detecting and identifying target proteins and nucleic acids in test samples.

In one embodiment, the invention provides a method for detecting a target protein or nucleic acid in a test sample that involves contacting a peptide-based reagent with a test sample and detecting whether the peptide-based reagent has bound to a target protein or nucleic acid from the test sample. When the peptide-based reagent has an antigen-recognizing peptide as its interactive domain, the detection method is conducted at a temperature, for a time and under conditions sufficient for antigen-antibody interaction. Such temperatures, times and conditions and can be readily determined by persons skilled in the art. For example, the peptide-based reagent can be incubated with a sample comprising a protein or nucleic acid extract at temperatures ranging from about 4° C. to about 42° C., for a time ranging from about 5 minutes to about 24 hours in an appropriately buffered solution. The presence or amount of a complex formed between the peptide-based reagent and the protein or nucleic acid is then determined or detected, e.g., through determination or detection of a label attached to the peptide-based reagent.

The peptide-based reagents of the invention can be adapted for use in any immunoassay known to one of skill in the art. For example, the peptide-based reagents can be used in procedures such as those involving radioimmunoassay, ELISA, or an immunofluorescence assay. Thus, for example, immunoassays that can be adapted for use with the present peptide-based reagents include those described in U.S. Pat. Nos. 3,791,932; 3,817837; 3,839,153; 3,850,752; 3,850,578; 3,853,987; 3,867,517; 3,879,262; 3,901,654; 3,935,074; 3,984,533; 3,996,345; 4,034,074; and 4,098,876.

Detection or measurement of formation of a complex between a peptide-based reagent and a target protein or nucleic acid can include detection of a label, reporter molecule or other detectable moiety. Such a label, reporter molecule or detectable moiety may be bound to the peptide-based reagent or to the pool of target proteins or nucleic acids.

Test samples which can be used in the present procedures include, for example, physiological fluids and samples from humans or animals, food samples, water, soil, as well as samples taken from work areas, counter-tops, shelving, storage areas for food, animal or poultry pens, or from the skin, hair, or surface of an animal. Such applications include human disease state testing.

The detection devices of the invention include a peptide-based reagent that is stably associated or linked to a solid support. The solid can be any useful support known to one of skill in the art. For example, the solid support can be a bead, filter, microtiter dish, or a biosensor chip.

The invention also comprises reagents and kits that include a device or container having one of the present peptide-based reagents. The reagent or kit can include a biosensor having the peptide-based reagent, or a test tube, microtiter plate or other object for conducting a detection procedure. The kit can contain control samples that are relevant to the test, procedure or device for which the kit is designed to facilitate. The kit can also contain solutions for conducting the methods of the invention, for example, solutions for diluting test samples, for incubating test samples with the biosensor or detection device, and for washing off any unbound test sample. The kit may also comprise a blocking agent that is contacted with the biosensor or detection device prior to or during contact with the sample. Desired control and other solutions are sterile and free of substances that may interfere with binding by the peptide-based reagent.

A label or reporter molecule that permits the detection of a complex formed between the target protein or nucleic acid and the peptide-based reagent can also be provided with any of the kits of the invention. Such a label or reporter molecule can be packaged separately from the biosensor, detection device or peptide-based reagent.

Labeled Peptide-Based Reagents

The invention also provides labeled peptide-based reagents. Labels that may be employed include radionuclides, fluorescent labels, chemiluminescent labels, calorimetric dyes, enzymes, enzyme substrates, enzyme cofactors, enzyme inhibitors, enzyme subunits, metal ions, particles, and the like. Radioisotopes commonly used as reporter molecules or labels include $^{32}P$, $^{125}I$ and $^{131}I$. Enzymes commonly used as reporter molecules or labels include enzymes such as alkaline phosphatase, horseradish peroxidase, beta-D-galactosidase and glucose oxidase. Commonly used fluorescent reporter molecules or labels include, for example, dyes such as fluorescein isothiocyanate (FITC), fluorescein, rhodamine, rhodamine B isothiocyanate (RITC), tetramethylrhodamine isothiocyanate (TRITC), 4,4'-diisothiocyanostilbene-2,2'-disulfonic acid (DIDS). See, for example, U.S. Pat. Nos. 3,766,162; 3,791, 932; 3,817,837; and 4,233,402. Other commonly used types of labels or reporter molecules include Texas red, phycoerythrin, umbelliferone, luminol, NADPH, and the like.

Various techniques can be employed for detecting and quantifying the presence of the label that are dependent upon the nature of the label. For fluorescent labels, a large number of different fluorometers and fluorescent microscopes are available. For chemiluminescent labels, luminometers or films are available. Enzymes producing a fluorescent, chemiluminescent, or colored product can be detected fluorometrically, luminometrically, spectrophotometrically or visually. Such labels can be employed in immunoassays and hybridization assays described herein.

Many procedures are available to one of skill in the art for attaching labels to peptides and/or nucleic acids. Examples of procedure for attaching labels to nucleic acids have been reported, for example, in Leary et al., Proc. Natl. Acad. Sci. (ISA) (1983) 80:4045; Renz and Kurz, Nucl. Acid Res. (1984) 12:3435; Richardson and Gumport, Nucl. Acid Res. (1983) 11:6167; Smith et al., Nucl. Acid Res. (1985) 13:2399; and Meinkoth and Wahl, Anal, Biochem. (1984) 138:267. The labels may be bound to a peptide-based reagent via a carboxy, thiol, amine, hydrazine or other functionality without detrimentally affecting peptide function or peptide binding to target.

The invention will be further described by the following examples.

EXAMPLE

This example describes the generation of a peptide backbone from a small stable peptide called Avian Pancreatic Polypeptide, as well as the design and construction of a DNA sequence to produce the new peptide. A computer program is also described that can be used to discover peptide sequences that can be inserted into the parental peptide backbone to produce specific antigen binding elements. One example is provided that shows that a recombinant modular antigen recognition molecule can be produced that binds to bovine pancreatic trypsin.

Materials and Methods

Bacterial growth conditions and culturing were performed as described by Miller (1972). Unless otherwise noted all procedures performed in this study were according to Maniatis et al. (1982) or Sambrook et al. (1989); including, agarose gel electrophoresis, and restriction endonuclease digestions. Vent™ DNA polymerase used in all PCR reactions was purchased from New England Biolabs and was used with the supplied buffer. DNA sequencing (Sanger et al., 1977) was performed using an Applied Biosystems, Inc. automated sequencer, and was performed by Genosys, Inc. DNA oligonucleotides were synthesized by Genosys, Inc. Protein concentration was determined according to the method of Bradford (1976) using bovine serum albumin (BSA) as a standard. Analytical gel filtration experiments were performed according to Siegel and Monty (1966) using a 7×250 mm BioSelect SEC-125 column from BioRad, Inc. All bacterial strains were purchased from the New England Biolabs, Inc. Protein SDS PAGE gels were made, run, and processed as per Laemmli (1970). Chemical reagents and chromatography resins were from Sigma Chemical Co. (St. Louis, Mo.), except where specifically noted.

Molecular Modeling

Molecular modeling utilized two visualization programs, Swiss PDB Viewer (Guex and Peitsch, 1997) and Rasmol (Sayle and Milner-White, 1995). Model work was performed on a Compaq PC running Windows 2000, as well as a Silicon Graphics, Inc. Octane UNIX workstation. Additionally, the Cerius2 molecular package from Molecular Simulations, Inc. was utilized on the Octane. The three dimensional structure file that was used to initiate the modeling study was downloaded from the Protein Databank (file 1PPT.ENT). Several successive rounds of amino acid deletions and substitutions were made in order to transform the wild-type APP molecule into a modular peptide that was suitable for diagnostic applications.

The final model was then subjected to energy minimization using a GROMOS 96 forcefield, and several rounds of molecular mechanics geometry optimization using the SYBYL forcefield (Clark et al., 1989). The final minimized/optimized model was then analyzed for bad sidechain interactions and torsional geometry. The finalized protein, and the three-dimensional model, were designated SAP. This is short for Synthetic (it is based on homology modeling) Antibody Peptide. SAP is the parental molecule into which can be inserted the specific 6-mer binding sequences.

Gene Design, Construction, and Cloning

The final SAP amino acid sequence was back translated using the standard genetic code. Codon choice was based on E. coli codon bias, meaning that final codon selected for a particular amino acid was the most frequently, or next highest used codon for that amino acid in E. coli. The full-length structural gene was 111 bp (including the stop codon). In order to build the gene sequence, ten single stranded oligonucleotides that span the coding region were synthesized. The oligonucleotides varied from 18 to 28 nucleotides in length. Each oligonucleotide was complementary to another oligonucleotide, such that when hybridized with the binding partner, the resulting fragment contained a central duplex region that was flanked on each end by a single-stranded region of eight nucleotides. Oligonucleotide sequences are shown in Table 3.

The construction of the gene encompassed three separate steps. First, 5 µg of each oligonucleotide and its complementary binding partner (for five separate reactions) were mixed together in 10 mM Tris-HCl (pH 7.2), 10 mM NaCl in a final volume of 10 µL. The specific oligonucleotide hybridizations were (see Table 3): (1a and 1b), (2a and 2b), (3a and 3b), (4a and 4b), and (5a and 5b). The mixture was heated in a waterbath at 95° C. for 10 minutes. The heat was turned off, and the entire waterbath was allowed to cool to room temperature over a period of five hours. Second, aliquots (10 µL) from each of the five "slow cool" reactions were mixed together (final volume 50 µL). The tube was heated at 45° C. for 10 minutes and then was placed into an ice bath. T4 DNA ligase and buffer (New England Biolabs) were added to the tube, and the reaction (final volume 60 µL) was incubated at 16° C. for 20 hours. Third, the full-length structural gene was selected from the mixture of fragments using two PCR primers (Table 3, 6a and 6b) that were complimentary to the extreme 5' and 3' ends of the structural gene. This ensured that only full-length gene product would be amplified. The PCR reaction was performed using 1 µL of the ligation mixture as follows: 95° C. for 1 minute; 49° C. for 1 minute; 72° C. for 30 seconds. Thirty cycles of this program were performed in a Techne Progene PCR device. A ten minute 72° C. extension incubation was performed after the last PCR cycle. The PCR reaction product was verified by DNA agarose gel electrophoresis.

The PCR reaction product was purified via a Promega DNA Wizard PCR clean-up kit and was prepared for cloning. First, the DNA fragment was treated with T4 DNA polymerase in the presence of ATP in order to ensure fully duplex ends. This reaction was performed according to the instructions from New England Biolabs, Inc. The DNA was re-purified using the Promega DNA Wizard PCR clean-up kit. Second, the DNA was digested with Nde I and Bam HI and was purified by ethanol precipitation. The final DNA was resuspended in a small volume of 10 mM Tris-HCl (pH 8.0), 1 mM EDTA.

The cloning vector, pET11a (Novagen), was digested with Nde I and Bam HI, and was purified using the Promega DNA clean-up kit. This digest produced a linear vector that contained ends that were compatible with DNA fragment. This combination ensured directional, in-frame cloning of the fragment. The vector and the insert were mixed in approximately 1:15 molar ratio and were ligated together in the presence of T4 DNA ligase at 16° C. for 20 hours (total reaction volume was 20 µL). Competent JM109 bacteria were transformed with 5 µL of the ligation reaction. After growth on LB/60 µg/mL ampicilin agar plates, single colonies were selected, and plasmid was purified from the colonies by the miniprep procedure using a Promega miniprep DNA isolation kit. Isolated plasmids were evaluated by DNA agarose gel electrophoresis, restriction endonuclease digestion, and finally by DNA sequencing. The plasmid construct was designated pSAPe.

Purification of SAP

The expression strategy utilized the T7 RNA polymerase over expression system from Novagen. Expression plasmid construct containing BL21(DE3) cells were grown at 37° C. in Luria broth supplemented with 0.5% glucose and 60 µg/mL ampicilin from a 1% inoculum. IPTG was added to a final concentration of 0.5 mM when the cells had reached an $A_{595}$ value of 0.8 (in approximately three hours post inoculation). Cell growth continued for five additional hours before harvesting. Typically, 5 g of cells was obtained per liter.

Cells were pelleted by centrifugation at 10,000×g for ten minutes and resuspended in one volume of 10 mM Tris-HCl, pH 8.0. The cells were respun as above and were frozen for at least 2 hours at −70° C. The frozen pellet was resuspended in two volumes of 10 mM Tris-HCl, pH 8.0. The mixture was lysed in a French Press (one pass, 20,000 psi). The resulting extract was clarified by centrifugation at 12,000×g for 20 minutes, and the supernatant was dialyzed against 20 mM Tris-HCl (pH 7.4), 100 mM NaCl, 1 mM EDTA (Buffer I). The dialyzed material was diluted to a final concentration of 2.5 mg/mL with Buffer I, and was designated as Fraction I. All subsequent chromatography steps were performed at room temperature in 10 mM Tris-HCl (pH 8.0), 1 mM EDTA.

Fraction I was applied to a 5 cm×1.8 cc² Mono-Q ion exchange column. A gradient was applied to the bound material as follows: buffer only, 40 mLs; followed by 100 mM NaCl, 40 mLs; and a linear gradient from 100 mM to 500 mM NaCl, 200 mLs. The APP peptide (and variants) eluted from the column approximately 50% through the gradient. Protein content in the fractions was visualized by SDS PAGE and fractions containing APP were pooled, dialyzed against 10 mM Tris-HCl (pH 8.0), 1 mM EDTA, and were concentrated to 10 mg/mL by pressure filtration through a semi permeable membrane (Amicon). The final concentrated pooled material was designated as Fraction II.

Fraction II was applied to a Sephadex G-75 column (110 cm×7.6 cc²). Peak fractions identified by SDS PAGE visualization were pooled. The G75 pool was designated as Fraction III. This Fraction contained homogeneous APP peptide and was used for all described experiments.

Production of SAP-2

A portion of the recognition sequence from Bovine Pancreatic Trypsin Inhibitor (PYRIRF, residues 561 to 566 in the molecule, SEQ ID NO:15) was converted into the DNA sequence 5'-CCGTATCGCATCCGCTTT (SEQ ID NO:16) using E. coli codon usage. A double stranded sequence was produced using procedures described above with flanking Sma I sites:

SEQ ID NO:17
5'-CCCGGGCCGTATCGCATCCGCTTTCCCGGG
GGGCCCGGCATAGCGTAGGCGAAAGGGCCC-5'

The SEQ ID NO:17 duplex DNA was digested with Sma I and was cloned into Sma I digested, dephosphorylated pSAPe. Recombinant clones were verified by DNA sequencing. The SAP-2 (SEQ ID NO:21) peptide was expressed and purified as above.

New Peptide Discovery

A FORTRAN 90 program was written to produce libraries of degenerate peptides. The code allows for the user to pick the length of the peptide (1–6 amino acids), how many amino acid substitutions can occur at each position (0 to 20), and whether or not the user wanted to randomly pick a certain percentage of all the possible peptides to write out to the final structure file. This last feature is used to limit file size and library complexity. The out put of the program, called MKPEPS, is a single file that contains the XYZ coordinates of all nonhydrogen atoms in the protein. This peptide library file is then used as input to a docking program (the MSI program LigandFit was used, although any available molecular docking program is fine). The docking program fits each peptide to a search zone on the target protein and outputs the fit score. The output file is rank ordered and the top scoring peptides are potentially strong binders. One such peptide library was run against bovine pancreatic trypsin. The top scoring peptide, YKLKY (SEQ ID NO:18), was converted into the DNA sequence TATAAACTGAAGTAT (SEQ ID NO:19). Sma I flanking sequences were added and a duplex of the following structure was produced as above.

SEQ ID NO:20
5'-CCCGGGTATAAACTGAAGTATCCCGGG
GGGCCCATATTTGACTTCATAGGGCCC-5'

After Sma I digestion the insert was cloned into Sma I digested, dephosphorylated pSAPe. Clones were confirmed by DNA sequencing. SAP-3 peptide was purified as above.

Calorimetry

Isothermal titration calorimetry (ITC) was performed with a VP-ITC instrument from MicroCal, inc. Titrations were carried out by injecting 5 $\mu$L of an inhibitor solution (at concentration ranges from 0.5 mM to 2.0 mM) into the 1.4 mL stirred reaction cell. APP and APP derivatives ranged in concentration from 50 to 80 $\mu$M in the cell. Both the inhibitor and the enzyme were in 20 mM sodium cacodylate (pH 5.5–7.0), 40 mM NaCl, or 20 mM Tris-HCl (pH 7.0–7.5), 40 mM NaCl. Titrations were conducted between 20° C. and 40° C. Typical experimental conditions for the titrations were a 10 second injection period followed by a 240 second delay between injections for a total of 40 injections. Blank titrations of inhibitor into buffer were performed in order to correct for heats of dilution and mixing.

The independent set of multiple binding sites is the most common model for binding experiment evaluations. The analytical solution for the total heat is determined by (Freire et al., 1990):

$$Q = V\Delta H \left[ [L] + \frac{1 + [M]nK - \sqrt{(1 + [M]nK - [L]K)^2 + 4K[L]}}{2K} \right]$$

where Q is the total heat, V is the cell volume, $\Delta H$ is the enthalpy, M is the macromolecule concentration (the binding partner in the cell), n is the binding stoichiometry, L is the ligand concentration (the binding partner in the syringe), and K is the association constant. Data were fit to this model using Origin version 5 (MicroCal, Inc.).

The association constant is related to the van't Hoff enthalpy according to the following relationship:

$$\left(\frac{\partial \ln K}{\partial T}\right)_P = \frac{\Delta H_{VH}}{RT^2}$$

where by definition, $$K = e^{-\frac{\Delta G}{RT}}$$

The free energy of binding is related to the binding enthalpy by:

$$\Delta G = \Delta H - T\Delta S$$

or with the incorporation of heat capacity data according to the Gibbs-Helmholtz equation:

$$\Delta G_{bind}(T_0) = \Delta H(T_0) - T_0 \left[ \frac{(\Delta H_{(T)} - \Delta G_{(T)})}{T} + \Delta C_p \ln\left(\frac{T_0}{T}\right) \right]$$

where $\Delta G$ is the Gibbs free energy of binding, $T_0$ is the reference temperature, and $\Delta C_p$ is the heat capacity. The value of $\Delta C_p$ is calculated from determining the calorimetric enthalpy at two different temperatures:

$$\Delta C_P = \frac{\Delta H_{T2} - \Delta H_{T1}}{T_2 - T_1} = \frac{\Delta S_{T2} - \Delta S_{T1}}{\ln\left(\frac{T_2}{T_1}\right)}$$

By measuring the apparent enthalpy of binding in two different buffers of known enthalpy of ionization, it is possible to measure the net number of protons transferred during the binding events:

$$\Delta H_{app} = \Delta H_{cor} + n\Delta H_{ioniz}$$

where $\Delta H_{cor}$ is the actual heat of binding at the pH measured. The sign indicates the direction of proton transfer.

Surface Plasmon Resonance

The BiaCore, Inc. BiaCore-X surface plasmon resonance (SPR) device was utilized to measure the interaction between bovine pancreatic trypsin and SAP-1 or SAP-2. For these experiments a carboxymethyl dextran sensor chip (CM-5) was activated with 50 mM N-hydroxysuccinimide, 0.2 M N-ethyl-N'-(dimethylaminopropyl)-carbodiimide at a flow rate of 10 $\mu$L per minute for ten minutes. The thiol coupling agent PDEA (2-(2-pyridinyldithio)ethaneamine hydrochloride) at a concentration of 80 mM was passed over the activated surface at a flow rate of 10 $\mu$L per minute for five minutes. SAP-1 or SAP-2 at a concentration of 50 ng/$\mu$L was coupled to the activated surface at a flow rate of 10 $\mu$L per minute for ten minutes. The final surface was inactivated by flowing 50 mM 1-cysteine, 1 M NaCl at a rate of 10 $\mu$L per minute for five minutes over the sensor surface. Buffer was switched to phosphate buffered saline (PBS) and bovine pancreatic trypsin was flowed over the sensor surface at a rate of 20 $\mu$L per minute, and at concentrations that ranged from 1 to 100 nM.

For this reaction of the type, A+B⇌AB, where A is the free flowing ligand and B is the immobilized ligand, the change in the SPR signal (R) is proportional to formation (for the association phase) or to the dissociation (for the dissociation phase) of the complex AB. Hence the sensor response becomes (Morton et al., 1995):

$$R(t) = \frac{ck_a}{ck_a + k_d} R_{max}(1 - e^{-(ck_a+k_d)t}) + R_b$$

for the association phase. $R_{max}$ is the measured response if all of the binding sites in the bound species were occupied, c is the ligand concentration, and $R_b$ is the shift in the baseline signal upon ligand injection. The dissociation phase is evaluated by:

$$R(t) = R_0 e^{-k_d t}$$

where $R_0$ is the SPR signal at the start of dissociation. A FFT routine separately smoothed the association and dissociation portions of the binding isotherm. Final kinetic analysis (O'Shannessy et al., 1993) was performed using Origin from Microcal, Inc.

Chemical Denaturation

Stability measurements of the protein were performed by measuring protein unfolding in the presence of urea via intrinsic tryptophan fluorescence (Lakowicz, 1983) in a Shimadzu RF5301 fluorometer. The excitation and emission wavelengths were 295 nm and 340 nm respectively. Both excitation and emission monochrometer slits were set at 1.5 nm. Protein (20 μM) was mixed with increasing amounts of urea (in the concentration range of zero to 6.8 M), and the samples were incubated at room temperature for ten hours to ensure that unfolding equilibrium had been achieved. Relative fluorescence was converted into free energy values according to the relation (Pace et al., 1989):

$$\Delta G = -RT \ln\left[\left(\frac{y_f - y_i}{y_i - y_u}\right)\right]$$

where $y_f$ and $y_u$ are the relative fluorescence values for fully folded and fully unfolded DST respectively, $y_i$ is the relative fluorescence of the unfolding intermediates, T is the absolute temperature, and R is the gas constant. Linear regression and extrapolation of the relationship ΔG versus [urea] was employed to determine the free energy value in the absence of denaturant ($\Delta G_{H2O}$). Similarly, the fraction unfolded protein ($F_u$) was calculated from the fluorescence data according to the relation (Pace et al., 1989):

$$F_U = \left(\frac{y_f - y_i}{y_f - y_u}\right)$$

Results

Modeling of SAP resulted in several amino acid changes in order to engineer a molecule that was useful in diagnostic applications. The first change made was to substitute Tyr27 with Trp. This helped to repack the hydrophobic core and also provided a useful intrinsic spectroscopic probe. Gly1 was changed to Met-Cys. This alteration allows the molecule to be produced using recombinant methodology, where an initiating Met is required for transcription/translation in E. coli. The Cys residue was engineered to form a stabilizing disulfide bond with a second Cys added at position 30 (replacing Val30). Asp11 was replaced with Pro in order to form a more stable kink to the interhelical loop domain and as a way of introducing a unique Sma I site into the DNA sequence. Similarly Ala12 was altered to Gly in order to complete the Sma I site in the DNA sequence. The sequence RHRY was removed, as this sequence has been implicated in APP receptor binding. Two alanines were added to the end of the sequence in order to properly space and orient the terminal cysteine residue. This last Cys is used to sequester and properly orient the SAP peptide onto a gold or other surface as the basis of the diagnostic assay.

The starting wild-type APP sequence and the final SAP amino acid sequences are shown below. Altered residues are in bold. SAP is 35 residues in length.

SEQ ID NO:1

Wt APP: GPSQPTYPGD DAPVEDLIRF YDNLQQYLNV VTRHRY

SEQ ID NO:14

SAP: CPSQPTYPGD PGPVEDLIRF YDNLQQWLNC VTAAC

Many of the remaining amino acids make critical contacts in the peptide and play a role in maintaining stability and conformation in the peptide. FIG. 1 shows the final SAP amino acid sequence and the *E. coli* codon biased DNA sequence. All inserts will be made between residues P11 and G12, at the center of the loop region. This corresponds to insertions between nucleotides 36 and 37.

In order for this structural gene to be synthesized, a double stranded DNA sequence was made. To facilitate cloning into an expression vector, flanking restriction endonuclease sites were incorporated into the DNA sequence. The final double stranded DNA sequence for the SAP structural gene is shown in FIG. 2. Oligonucleotide pairs 1–6 shown in Table 3 were used to construct the DNA sequence shown in FIG. 2, where each oligonucleotide pair has an A and a B member.

TABLE 3

Oligonucleotide Pairs 1–6 Used for Gene Construction and PCR Reactions.

| Oligo Name | Oligo Sequence | SEQ ID NO: |
|---|---|---|
| Pair 1A | 5'-ACACACCATATGTGCCCGAG | 23 |
| Pair 1B | 5'-TCGGCTGGCTCGGGCACATATGGTGTGT | 24 |
| Pair 2A | 5'-CCAGCCGACCTATCCGGGCGATCCCGG | 25 |
| Pair 2B | 5'-CCACCGGCCCGGGATCGCCCGGATAGG | 26 |
| Pair 3A | 5'-GCCGGTGGAAGATCTGATCCGCTTTTAT | 27 |
| Pair 3B | 5'-AGGTTATCATAAAAGCGGATCAGATCTT | 28 |
| Pair 4A | 5'-GATAACCTGCAGCAGTGGCTGAACTGCG | 29 |
| Pair 4B | 5'-CGGCGGTCACGCAGTTCAGCCACTGCTGC | 30 |
| Pair 5A | 5'-TGACCGCCGCCTGCTAGGGATCCACACAC | 31 |
| Pair 5B | 5'-GTGTGTGGATCCCTAGCAGG | 32 |
| Pair 6A | 5'-ACACACCATATGTGCCCG | 33 |
| Pair 6B | 5'-GTGTGTGGATCCCTAGCA | 34 |

The final GROMOS energy minimized structure of SAP is shown in FIGS. 3–5. The amino acid changes do not result in a destabilized structure, and the added tryptophan adds hydrophobic character to the helical interface core. FIG. 5 shows the molecule with the three cysteines in space filling mode. An intramolecular disulfide bond is formed between Cys2 and Cys31. As will be shown below, this disulfide greatly increases the stability of SAP relative to wild-type APP. The SAP peptide, as well as the SAP-1 and SAP-2 variants are efficiently expressed and purified from *E. coli*. Typical yields (unoptimized) were approximately 15–25 mg/L.

Figure 6:
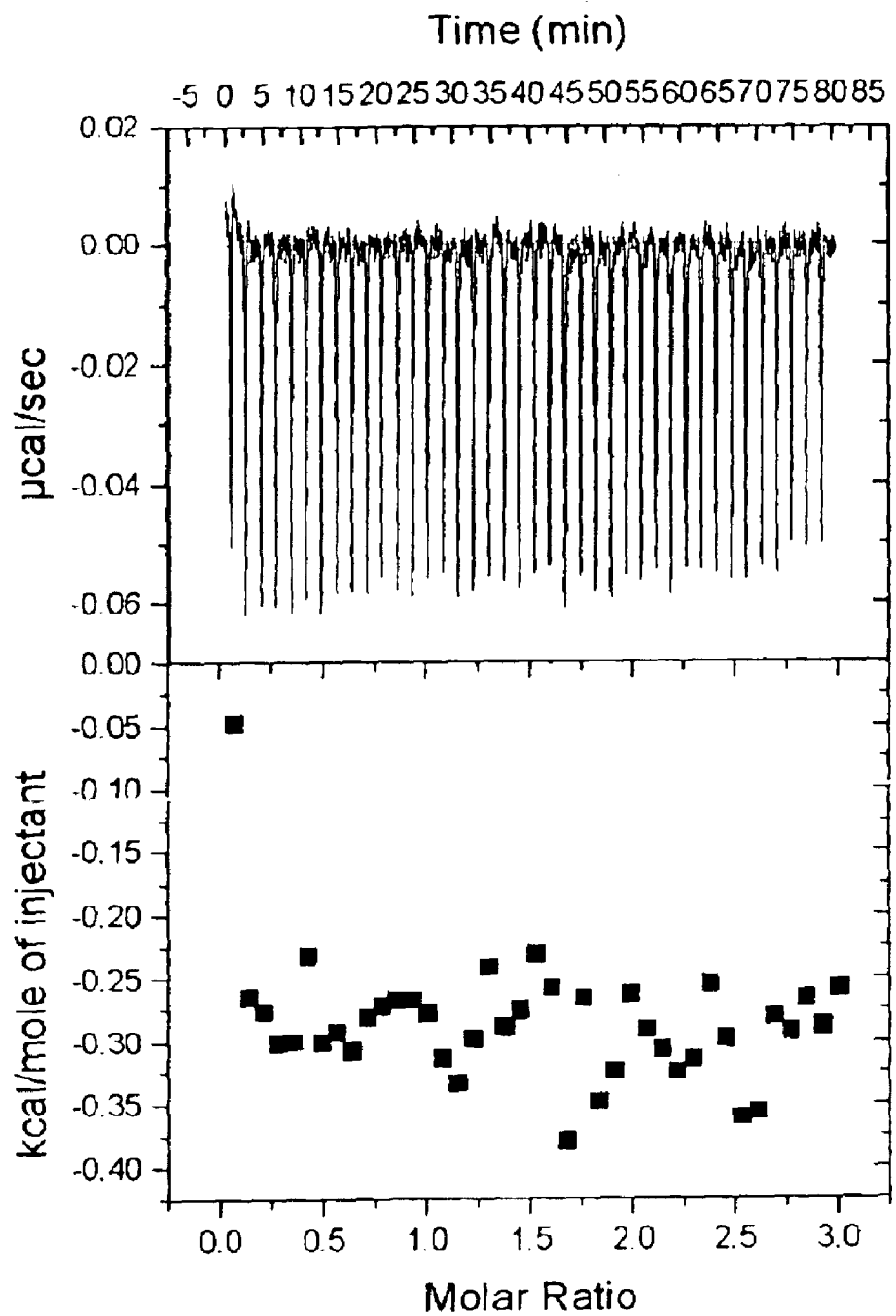
FIG. 6 provides an ITC analysis of the interaction between SAP and bovine pancreatic trypsin. SAP was dissolved in 20 mM cacodylate (pH 7.0), 20 mM NaCl at a final concentration of 2 mM. Trypsin was dialyzed into the same buffer and was used in the calorimeter cell at a concentration of 20 $\mu$M. No binding is evident throughout the titration. The temperature was maintained at 30° C. Forty injections of 5 $\mu$L each were employed with a 240 second re-equilibrium time between injections.

The ability of SAP, SAP-1, and SAP-2 to bind bovine pancreatic trypsin was measured by isothermal titration calorimetry (ITC). FIG. 6 clearly indicates that SAP has no natural binding affinity for trypsin. Under all experimental conditions, there is no detectable binding. SAP-1 on the other hand, shows remarkable binding specificity for trypsin, as is shown in FIG. 7.

Figure 7:
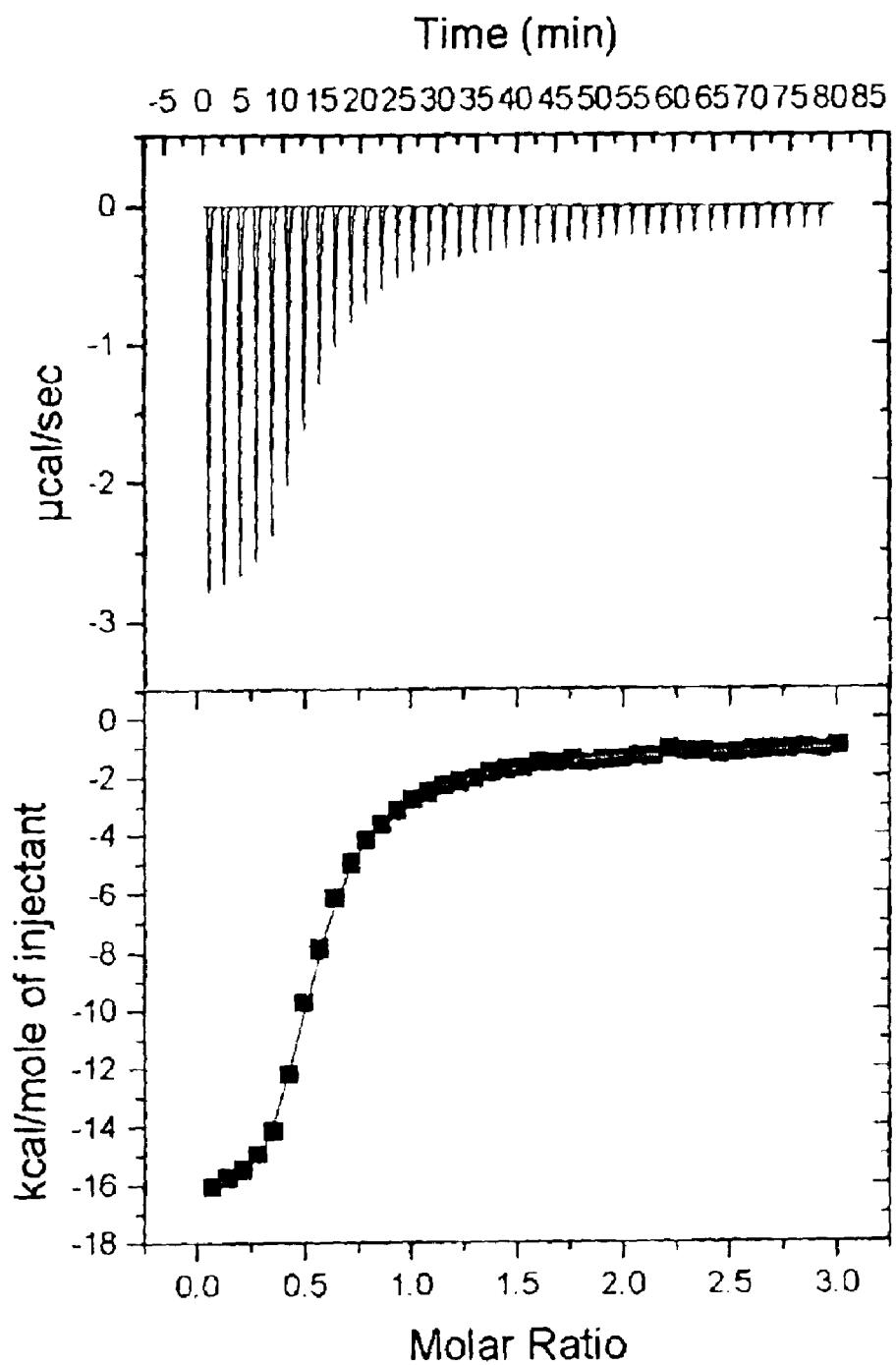
FIG. 7 provides an ITC analysis of the interaction between SAP-1 and bovine pancreatic trypsin. SAP-1 was dissolved in 20 mM cacadylate (pH 7.0), 20 mM NaCl at a final concentration of 1 mM. Trypsin was dialyzed into the same buffer and was used in the calorimeter cell at a concentration of 20 $\mu$M. The temperature was maintained at 20° C. Forty injections of 5 $\mu$L each were employed with a 240 second re-equilibrium time between injections.

The binding isotherm in FIG. 7 can be analyzed and the following thermodynamic parameters extracted:

| Stoichiometry: | 0.975 +/− 0.02 |
|---|---|
| ΔH (kcal/mol): | −26.1 +/− 1.45 |
| ΔS (cal mol$^{-1}$ K$^{-1}$) | −11.6 +/− 2.2 |
| $K_a$ (M$^{-1}$): | 1.65 × 10$^6$ +/− 4.5 × 10$^4$ |
| Temp (K) | 293 |

This result indicates that the interaction between the SAP-1 and trypsin is enthalpically driven, that is, that ΔH is negative. The reaction is not favored entropically as evidenced by the negative value of ΔS. However, the enthalpic term is larger in magnitude than the term, TΔS, hence the overall free energy (ΔG) is negative. Performing the binding reaction at a higher temperature returns the following thermodynamic parameters:

| Stoichiometry: | 0.99 +/− 0.03 |
|---|---|
| ΔH (kcal/mol): | −15.4 +/− 2.05 |
| ΔS (cal mol$^{-1}$ K$^{-1}$) | −21.1 +/− 1.8 |
| $K_a$ (M$^{-1}$): | 2.40 × 10$^6$ +/− 3.7 × 10$^4$ |
| Temp (K) | 303 |

Again the binding reaction is enthalpically favored, entropically unfavored and overall energetically favored. This results in a $\Delta C_p$ of −0.51 kcal/mol K indicating that the binding reaction buries a small amount of accessible surface area (ΔASA). These results show that the SAP molecule can serve as a functional binding reagent simply by inserting up to six amino acids into the center of the loop domain. The SAP reagent is modular in the sense that any combination of peptides can be used to alter or change binding specificity. The overall structure of the reagent does not change (the parental backbone), making it rather useful as a component in a broad range of diagnostic tests. The conservation of SAP structure is also an aid in purification and it standardizes shelf life and chemistries associated with linking the material to the surface of support material or beads in lateral flow diagnostic assays.

Figure 8:
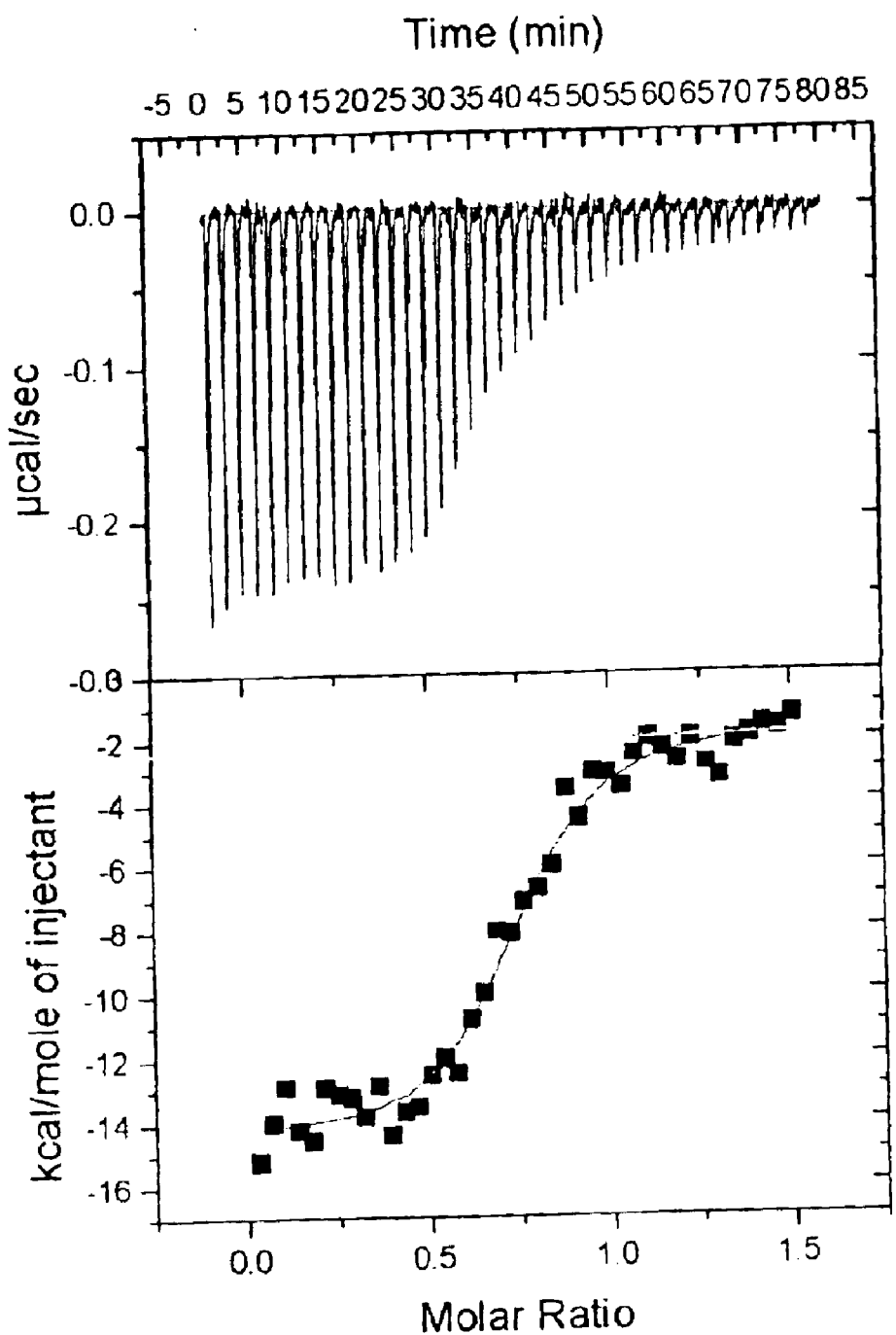
FIG. 8 provides an ITC analysis of the binding of recombinant SAP-2 to bovine pancreatic trypsin. Top panel: Raw ITC data for the titration of SAP-2 (1.0 mM) into trypsin (20 $\mu$M) in 20 mM cacadylate, pH 7.0 at 25° C. Each peak shows the heat produced by the injection and subsequent binding reaction. Bottom panel: Binding isotherm produced by integrating each injection peak with respect to time.

The interaction between bovine pancreatic trypsin and SAP-2 is shown in FIG. 8. The peptide insert, YKLKY (SEQ ID NO:18), shows binding to trypsin, although at a somewhat lower affinity than the peptide derived from bovine pancreatic trypsin inhibitor. Still it is possible to utilize the MKPEPS computer program (that creates user defined peptide library structure files) and automated molecular docking to design binding sequences de novo. Hence the SAP peptide can be used in conjunction with the modeling software to produce an infinite number of novel antigen (or analyte) binding reagents. The ITC isotherm shown in FIG. 8 can be used to produce the following thermodynamic parameters for the association of SAP-2 and trypsin.

| Stoichiometry: | 0.995 +/− 0.06 |
|---|---|
| ΔH (kcal/mol): | −31.2 +/− 2.30 |
| ΔS (cal mol$^{-1}$ K$^{-1}$) | −16.2 +/− 1.22 |
| $K_a$ (M$^{-1}$): | 6.4 × 10$^5$ +/− 5.3 × 10$^3$ |

It is a proof of concept that the enthalpically driven binding reaction, with a moderately high affinity constant, can be produced with the MKPEPS-SAP system without any optimization of the insert peptide sequence. It should be possible to raise the equilibrium affinity constant higher by performing targeted docking reactions with MKPEPS generated sequences clustered around YKLKY (SEQ ID NO:18) (or any other lead peptide insert sequence). It is also possible to utilize the SAP system with peptides derived from the scientific or patent literature, or using such molecular techniques as phage display.

Calorimetric analysis of SAP-1 and SAP-2 binding to bovine pancreatic trypsin inhibitor in different buffers indicates that no protons are transferred as a result of binding in the case of SAP-1 (n=0.01), but that one proton (n=1.12) is transferred from the protein to the peptide in the case of SAP-2 binding.

Figure 9:
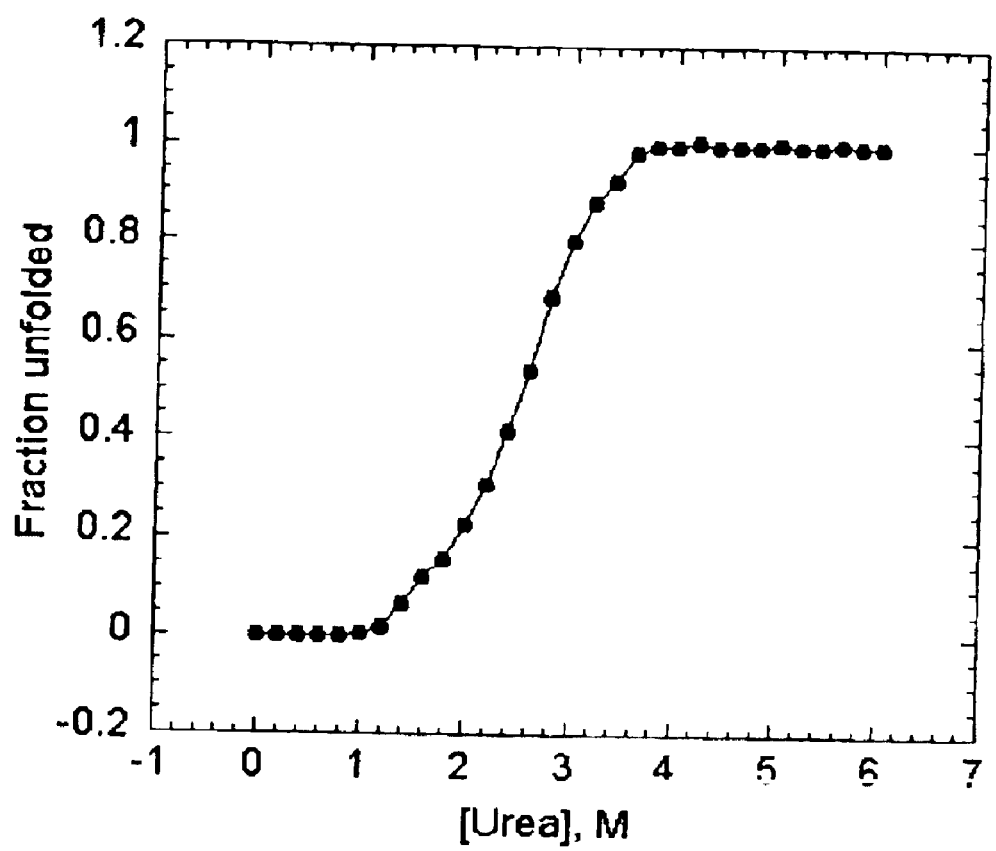
FIG. 9 graphically illustrates the unfolding of SAP in urea.

The stability of SAP was measured in the presence of urea, as is shown in FIG. 9. The unfolding curve corresponds to a native free energy of −3.1 kcal/mol and a $m_{1/2}$ value of 2.5 M urea. These numbers will serve as the basis for comparing loop insertion variants of SAP. The unfolding curve shows no dimerization phenomenon as has been evidenced for various pancreatic polypeptides (e.g.- Kanazawa and Hamaguchi, 1986; Chang et al., 1980; Noelken et al., 1980). Thus it is possible that one or several of the mutations made in the wild-type peptide results in fully monomeric peptide. This is a critical observation and a necessary requirement for a useful antibody-like diagnostic reagent. It is important that the antibody-like reagent that is being coupled to polystyrene or gold beads or to the capture zone in a lateral flow assay be monomeric and not be prone to multimerization.

Figure 10:
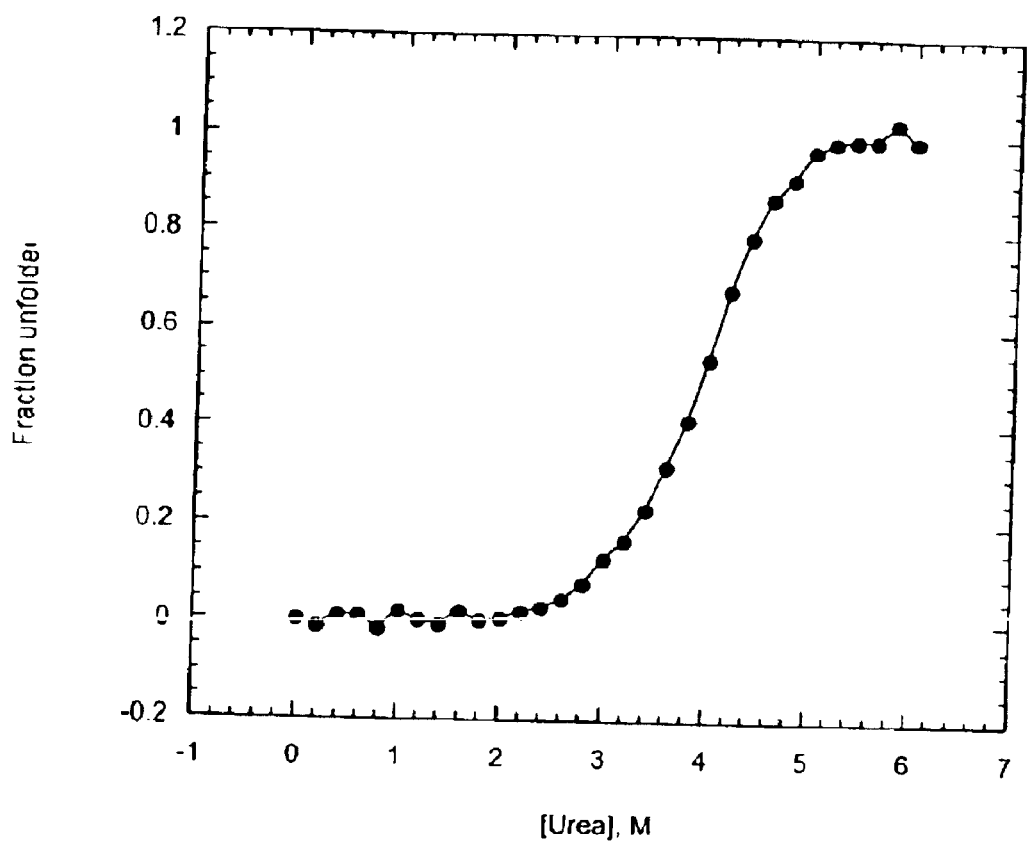
FIG. 10 graphically illustrates the unfolding of SAP-1 in urea.

Surprisingly SAP-1 is more stable than SAP by 2.0 kcal/mol. The structural reason for the free energy change is not immediately apparent from modeling. Attempts are currently underway to crystallize (Wood et al., 1977) this peptide in order to fully understand this phenomenon. Nonetheless, the stabilization provided by the loop insertion makes SAP-1 an even better diagnostic tool. As is shown in FIG. 10 SAP-1 has a native free energy of −5.1 kcal/mol and a corresponding $m_{1/2}$ value of 4.0 M urea.

Figure 11:
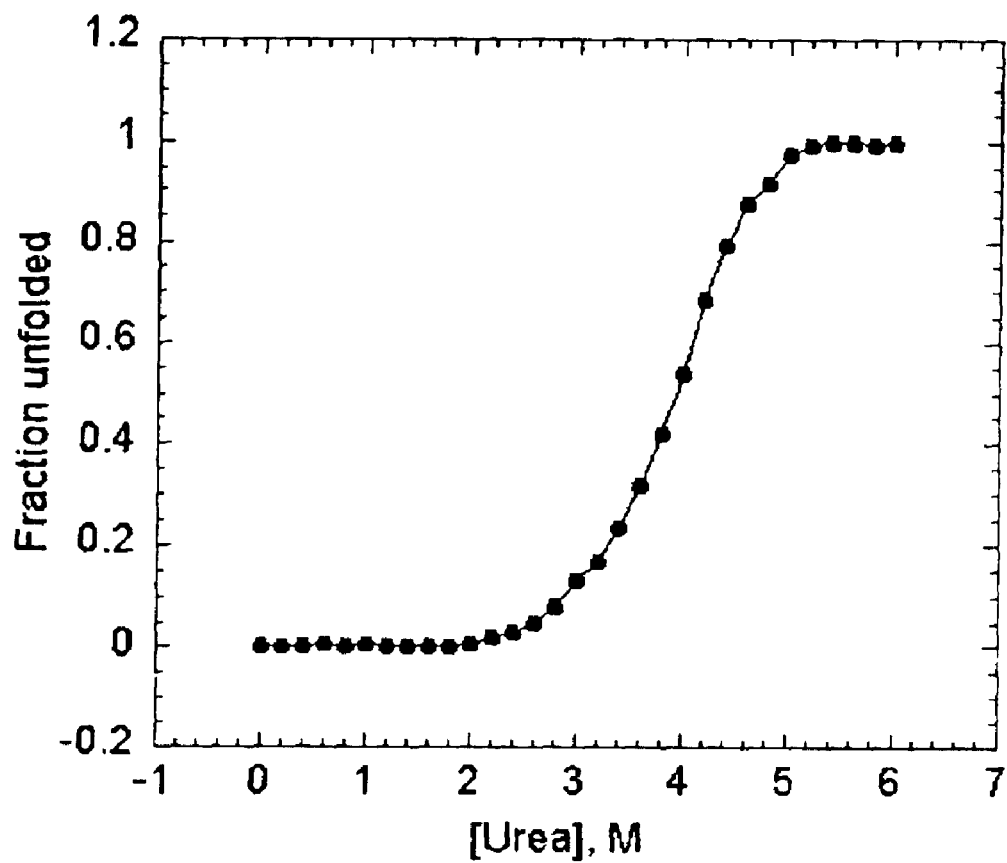
FIG. 11 graphically illustrates the unfolding of SAP-2 in urea.

A similar stabilization phenomenon is evidenced when SAP-2 is unfolded in the presence of urea. FIG. 11 shows the fraction unfolded as a function of urea concentration. Again analysis of the isotherm indicates that SAP-2 is stabilized in the native state by 2.1 kcal/mol relative to SAP (and 0.1 kcal/mol relative to SAP-1). The $m_{1/2}$ for the SAP-2 unfolding reaction is 4.05 M urea. The free energy relationships seen experimentally are only qualitatively mirrored in modeling of SAP, SAP-1 and SAP-2. Six amino acids in the inserted sequence appears to be the upper limit. Short-range effects such as solvent interactions that are not apparent from the molecular modeling may contribute to the stability of the peptide. Such stability is unusual in peptides of this size.

Figure 12:
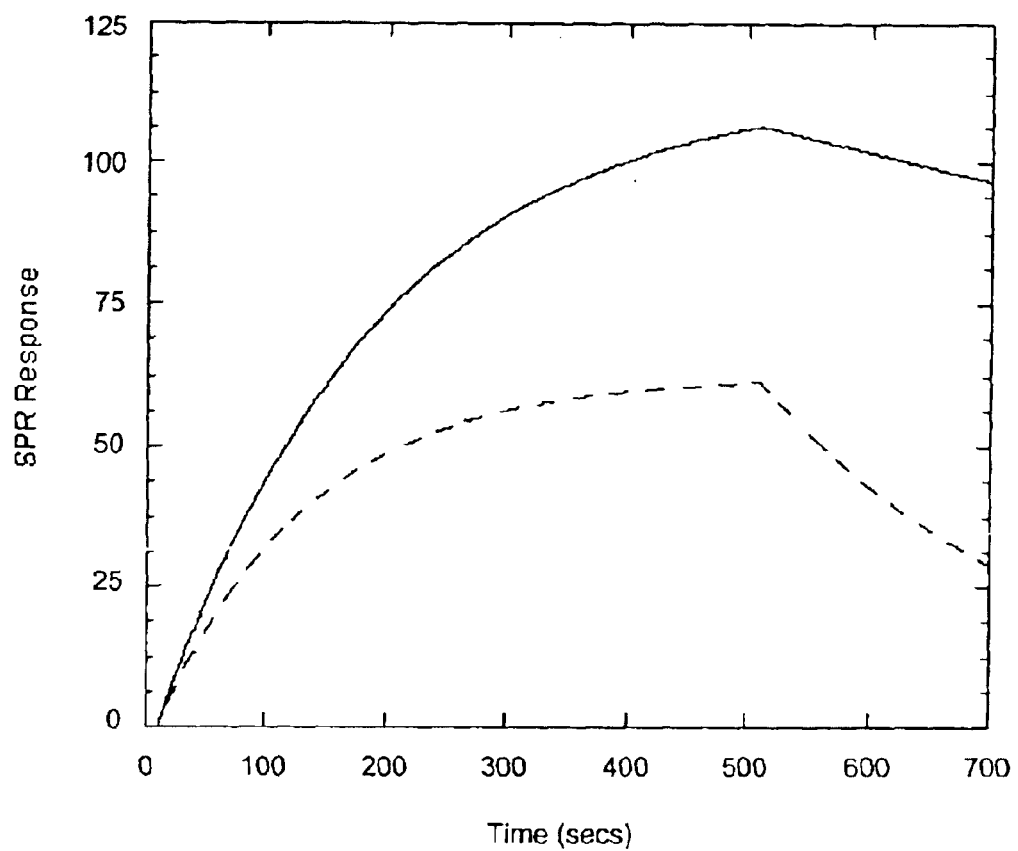
FIG. 12 provides surface plasmon binding isotherms for the association (0 to 500 seconds) and the dissociation (500 to 700 seconds) of bovine pancreatic trypsin with SAP-1 (solid line) and SAP-2 (dashed line).

The kinetics of SAP-1 and SAP-2 binding to bovine pancreatic trypsin mirror the thermodynamic relationships described by the ITC experiments. FIG. 12 shows binding isotherms of bovine pancreatic trypsin binding to a surface of SAP-1 or SAP-2. Kinetic rate constants for the SAP-1/ trypsin interaction are $1.3 \times 10^5$ (ka) and $1.7 \times 10^{-2}$ ($k_d$). The interaction between SAP-2 and trypsin indicate kinetic rate constants of $8.2 \times 10^4$ ($k_a$) and $6.9 \times 10^{-2}$ ($k_d$). The binding isotherms clearly show that SAP-1 and SAP-2 can be properly oriented on a surface via the C-terminal cysteine thiol in such a manner that they can still affect binding.

Peptide Libraries

The MKPEPS program is very versatile in creating libraries of peptides that serve as input to molecular docking programs. The libraries can range from fully random and totally represented, to targeted and partially represented. The randomness factor allows an experimenter to sample all or selected areas of sequence space. The representation factor reduces the total number of peptides in the final library by taking every ith peptide from a fully generated library (the culling factor). This reduces docking computation time. Careful selection of the MKPEPS library and choice of automated docking search zone criteria are instrumental in i) lowering overall computer time, ii) increasing the likelihood of meaningful hits (that is increase the correlation between docking score and the experimental equilibrium affinity constant), and iii) decreasing the reliance on such labor intensive methods as phage display.

The design criteria and flow of the MKPEPS program are shown in Table 4.

TABLE 4

Flow chart of MKPEPS program.

1) The main program is a shell script called mkpeps. It can be run with several specifiers. All of them fit within the following 4 versions:
    i) mkpeps     Runs @mkpeps
    ii) mkpeps class     Runs @outtags
    iii) mkpeps peps     Runs @outpeps
    iv) mkpeps help     Prints out a helpful message
2) There are three main programs compiled from Fortran code:
    @mkpeps:     generates an csd file of peptides according to user specifications
    @outtags:     prints out the possible tags/classes of residues used by @mkpeps
    @outpeps:     prints out the abbreviations for all 20 amino acids
3) The code directory contains the following files:
(Number of lines per program listed in the first column)
    59 classtags.f
    233 initaa.f
    101 initpeps.f
    101 libpeps.f
    23 mkpeps.f
    42 outaa.f
    229 outpep.f
    12 outpeps.f
    12 outtags.f
    46 ran3.f
    403 setup.f
    24 aa.h
    9 peps.h
    4 tags.h

1298 ==TOTAL

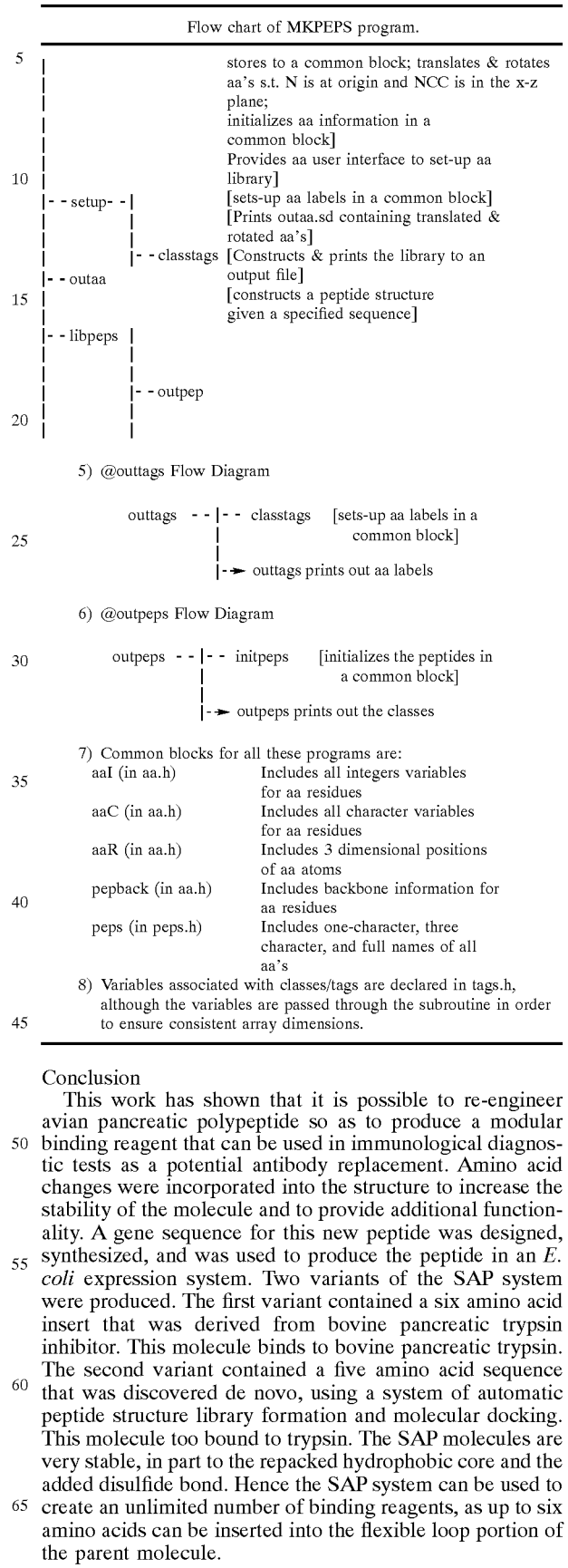

Conclusion

This work has shown that it is possible to re-engineer avian pancreatic polypeptide so as to produce a modular binding reagent that can be used in immunological diagnostic tests as a potential antibody replacement. Amino acid changes were incorporated into the structure to increase the stability of the molecule and to provide additional functionality. A gene sequence for this new peptide was designed, synthesized, and was used to produce the peptide in an *

Bibliography

Blundell, T L., Pitts, J E., Tickle, I J., Wood, S P., and Wu, C W., (1981), X-ray analysis (1.4 A resolution) of avian pancreatic polypeptide: Small globular protein hormone. Proc. Nat. Acad. Sci. USA. 78: 4175–79.

Bjornholm, B., and Jorgensen, F S., (1993), Conservation of a helix stabilizing dipole moment in the PP-fold family of regulatory peptides. Biochem. 32: 2954–59.

Bradford, M. M. (1976). A rapid and sensitive method for the quantitation of microgram quantities of protein utilizing the principle of dye binding. Anal. Biochem. 72, 248–254.

Cerda-Reverter, J. M., and Larhammar, D., 2000, Neuropeptide Y family of peptides: structure, anatomical expression, function, and molecular evolution, Biochem Cell Biol 78(3):371–92.

Clark, M., Cramer, R. D., and van Opdensch, N. (1989). J. Computational Chem. 10, 982–986.

Chang, P J., Noelken, M E., and Kimmel, J R., (1980), Reversible dimerization of avian pancreatic polypeptide. Biochem. 19:1844–49.

Freire, E., van Osdol, W W., Mayorga, O L, and Sanchez-Ruiz, J M. (1990). Calorimetrically determined dynamics of complex unfolding transitions in proteins. Annu Rev Biophys Biophys Chem. 19, 159–88.

Fuhlendorff, J., Johansen, N L., Melberg, S G., Thogersen, H., and Schwartz, T W. (1990), The antiparallel pancreatic polypeptide fold in the binding of neuropeptide Y to Y1 and Y2 receptors. J. Biol. Chem. 265: 11706–11712.

Gehlert, D R., Schober, D A., Beavers, L., Gadski, R., Hoffman, J A., Smiley, D L., Chance, R E., Lundell, I., Larhammar, D. (1996), Characterization of the peptide binding requirements for the cloned human pancreatic polypeptide-preferring receptor. Molec. Pharmacol. 50: 112–118.

Gingerich, R L., Akpan, J O., Gilbert, W R., Leith, K M., Hoffman, J A., and Chance, R E. (1991), Structural requirements of pancreatic polypeptide receptor binding. Am J Physiol. 261(3 Pt 1):E319–24.

Glover, I., Haneef, I., Pitts, J., Wood, S., Moss, D., Tickle, I., and Blundell, T., 1983, Conformational flexibility in a small globular hormone: x-ray analysis of avian pancreatic polypeptide at 0.98-A resolution, Biopolymers 22(1):293–304.

Griko, Y V, and Kapanadze, M D. (1995), Purification and characterization of human pancreatic polypeptide expressed in *E. coli*. Biochem. And Biophys. Res. Commun. 213: 239–248.

Guex, N. and Peitsch, M. C. (1997). Swiss Model and the Swiss-Pdb Viewer: An environment for comparative protein modeling. Electrophoresis 18, 2714–2723.

Hazelwood, R L., (1990), Pancreatic polypeptide (PP) and its relevant relatives, in Prog. Comparat. Endocrinol. Wiley and Sons, p. 250–56.

Kanazawa, I., and Hamaguchi, K., (1986), Unfolding by temperature and guanidine hydrochloride of chicken pancreatic polypeptide. J. Biochem. 100: 207–212.

Karlsson, R., and Falt, A. (1997). Experimental design for kinetic analysis of protein-protein interactions with surface plasmon resonance biosensors. J. Immunol. Meths. 200, 121–33.

Kruger, P., Strassburger, W., Wollmer, A., and van Gunsteren, W. F., 1985, A comparison of the structure and dynamics of avian pancreatic polypeptide hormone in solution and in the crystal, Eur Biophys J 13(2):77–88.

Laemmli, U. K. (1970). Cleavage of structural proteins during the assembly of the head of bacteriophage T4. Nature (London) 227, 680–685.

MacKerell, A D, (1991), Molecular Modeling and dynamics of biologically active peptides: Application to Neuropeptide Y. Methods in Enzymol. 202: 449–470.

Maniatis, T., Fritch, E. F., and Sambrook, J. (1981). Molecular Cloning: A Laboratory Manual, Cold Spring Harbor Laboratory, Cold Spring Harbor, N.Y.

Miller, J. H. (1972). Experiments in Molecular Genetics. Cold Spring Harbor Laboratory, Cold Spring Harbor, N.Y.

Noelken, M E., Chang, P J., and Kimmel, J R., (1980), Conformation and association of pancreatic polypeptide from three species. Biochem. 19: 1838–1843.

O'Shannessy, D. J., Brigham-Burke, M., Soneson, K. K, Hensley, P., and Brooks, I. (1993). Determination of rate and equilibrium binding constants for macromolecular interactions using surface plasmon resonance: use of non linear least squares analysis methods. Anal. Biochem. 212, 457–468.

Pace, C. N., Shirley, B. A., and Thomson, J. A. (1989). In Protein Structure a practical approach (T. E. Creighton, Ed.), pp. 311–330. IRL Press, Oxford, UK.

Sambrook, J., Fritch, E F., and Maniatis, T. (1989). Molecular Cloning: A Laboratory Manual, $2^{nd}$ ed., Cold Spring Harbor Laboratory, Cold Spring Harbor, N.Y.

Sanger, F., Nicklen, S., and Coulson, A. R. (1977). DNA sequencing with chain terminating inhibitors. Proc. Nat. Acad. Sci. U.S.A. 74, 5643–5647.

Sayle, R. A. and Milner-White, E. J. (1995). RasMol: Biomolecular graphics for all. Trends in Biochemical Sciences 20, 374–376.

Siegel, L M., and Monty, K J. (1966). Determination of molecular weights and frictional ratios of proteins in impure systems by the use of gel filtration and density gradient centrifugation. Application to crude preparations of sulfite and hydroxylamine reductases. Biochim. Biophys. Acta 112, 346–362.

Wood, S P., Pitts, J E., Blundell, T L., Tickle, I J., and Jenkins, J A., (1977), Purification, crystallization and preliminary X-ray studies on avian pancreatic polypeptide. Eur. J. Biochem. 78: 119–26.

Zondlo, N J, and Schepartz, A. (1999), Highly specific DNA recognition by a designed miniature protein. J. Am. Chem. Soc. 121: 6938–39.

---

What is claimed is:

1. A peptide-based reagent comprising a peptide backbone and an interactive domain, where the peptide backbone is a peptide comprising any one of SEQ ID NO:2–6, 8–11 or 14.

2. The peptide-based reagent of claim 1 wherein the peptide backbone has a polyproline helix, a short loop region, and an alpha helix, and wherein the peptide backbone folds so that the polyproline helix and the alpha helix hydrophobically interact.

3. The peptide-based reagent of claim 1 wherein the interactive domain is a binding domain, an inhibitor domain, an antigen-recognizing peptide, a linker, a label, a solid support, or an enzymatic active site.

4. The peptide-based reagent of claim 1 wherein the interactive domain is a peptide comprising SEQ ID NO:18.

5. A peptide-based reagent comprising a peptide backbone and an interactive domain, where the peptide backbone is a peptide comprising SEQ ID NO:11 or 14.

6. The peptide-based reagent of claim 5 wherein the peptide backbone has a polyproline helix, a short loop region, and an alpha helix, and wherein the peptide backbone folds so that the polyproline helix and the alpha helix hydrophobically interact.

7. The peptide-based reagent of claim 5 wherein the peptide backbone is folded and further stabilized by a disulfide bond.

8. The peptide-based reagent of claim 5 wherein the interactive domain is a binding domain, an inhibitor domain, an antigen-recognizing peptide, a linker, a label, a solid support, or an enzymatic active site.

9. The peptide-based reagent of claim 5 wherein the interactive domain is a peptide comprising SEQ ID NO:18.

* * * * *